US009855040B2

(12) United States Patent
Kostrzewski

(10) Patent No.: US 9,855,040 B2
(45) Date of Patent: Jan. 2, 2018

(54) SURGICAL STAPLING LOADING UNIT HAVING ARTICULATING JAWS

(71) Applicant: Covidien LP, Mansfield, MA (US)

(72) Inventor: Stanislaw Kostrzewski, Newtown, CT (US)

(73) Assignee: Covidien LP, Mansfield, MA (US)

( * ) Notice: Subject to any disclaimer, the term of this patent is extended or adjusted under 35 U.S.C. 154(b) by 483 days.

(21) Appl. No.: 14/638,482

(22) Filed: Mar. 4, 2015

(65) Prior Publication Data

US 2016/0256152 A1 Sep. 8, 2016

(51) Int. Cl.

| A61B 17/068 | (2006.01) |
|---|---|
| A61B 17/072 | (2006.01) |
| A61B 17/42 | (2006.01) |
| B25J 15/00 | (2006.01) |
| A61B 17/00 | (2006.01) |
| A61B 17/29 | (2006.01) |

(52) U.S. Cl.
CPC ...... *A61B 17/068* (2013.01); *A61B 17/00234* (2013.01); *A61B 17/07207* (2013.01); *A61B 17/42* (2013.01); *B25J 15/0019* (2013.01); *B25J 15/0028* (2013.01); *A61B 2017/0046* (2013.01); *A61B 2017/00296* (2013.01); *A61B 2017/00473* (2013.01); *A61B 2017/00477* (2013.01); *A61B 2017/07228* (2013.01); *A61B 2017/07271* (2013.01); *A61B 2017/2927* (2013.01); *A61B 2017/2931* (2013.01); *A61B 2017/2932* (2013.01); *A61B 2017/2933* (2013.01); *A61B 2017/2941* (2013.01); *A61B 2017/2944* (2013.01); *A61B 2017/2946* (2013.01); *A61B 2017/4216* (2013.01)

(58) Field of Classification Search
CPC ............ A61B 17/068; A61B 17/00234; A61B 17/07207; A61B 2017/00367; A61B 2017/07214
USPC .................................................. 606/129, 153
See application file for complete search history.

(56) References Cited

U.S. PATENT DOCUMENTS

| 2,891,250 A | 6/1959 | Hirata |
| 3,080,564 A | 3/1963 | Strekopitov et al. |

(Continued)

FOREIGN PATENT DOCUMENTS

| EP | 0503662 A1 | 9/1992 |
| EP | 2617369 A1 | 7/2013 |

(Continued)

OTHER PUBLICATIONS

European Search Report dated Jul. 8, 2016, issued in EP Application No. 16158408.1.

(Continued)

*Primary Examiner* — Stephen F Gerrity
*Assistant Examiner* — Jeffrey T Ice

(57) ABSTRACT

An end effector includes first and second jaw members that are pivotable relative to one another between open and clamped configurations about a pivot axis. The first and second jaw members each define a pivot hole which defines the pivot axis. The first and second jaw members also each define an articulation axis that is orthogonal to the pivot axis and position distal of the pivot axis. The first and second jaw members are articulatable about the articulation axis between straight and fully articulated configurations.

24 Claims, 29 Drawing Sheets

(56) References Cited

U.S. PATENT DOCUMENTS

| | | | |
|---|---|---|---|
| 3,252,643 A | 5/1966 | Strekopov et al. |
| 3,269,630 A | 8/1966 | Fleischer |
| 3,275,211 A | 9/1966 | Hirsch et al. |
| 3,315,863 A | 4/1967 | O'Dea |
| 3,494,533 A | 2/1970 | Green et al. |
| 3,589,589 A | 6/1971 | Akopov |
| 3,692,224 A | 9/1972 | Astafiev et al. |
| 3,795,034 A | 3/1974 | Strekopytov et al. |
| 3,822,818 A | 7/1974 | Strekopytov et al. |
| 3,935,981 A | 2/1976 | Akopov et al. |
| 3,949,923 A | 4/1976 | Akopov et al. |
| 4,047,654 A | 9/1977 | Alvarado |
| 4,216,891 A | 8/1980 | Behlke |
| 4,244,372 A | 1/1981 | Kapitanov et al. |
| 4,296,881 A | 10/1981 | Lee |
| 4,305,539 A | 12/1981 | Korolkov et al. |
| 4,354,628 A | 10/1982 | Green |
| 4,378,901 A | 4/1983 | Akopov et al. |
| 4,383,634 A | 5/1983 | Green |
| 4,402,444 A | 9/1983 | Green |
| 4,415,112 A | 11/1983 | Green |
| D273,513 S | 4/1984 | Spreckelmeier |
| 4,442,964 A | 4/1984 | Becht |
| 4,470,533 A | 9/1984 | Schuler |
| 4,475,679 A | 10/1984 | Fleury, Jr. |
| 4,485,811 A | 12/1984 | Chernousov et al. |
| 4,506,670 A | 3/1985 | Crossley |
| 4,506,671 A | 3/1985 | Green |
| 4,508,253 A | 4/1985 | Green |
| 4,522,327 A | 6/1985 | Korthoff et al. |
| 4,527,724 A | 7/1985 | Chow et al. |
| 4,530,453 A | 7/1985 | Green |
| 4,550,870 A | 11/1985 | Krumme et al. |
| 4,566,620 A | 1/1986 | Green et al. |
| 4,568,009 A | 2/1986 | Green |
| 4,573,622 A | 3/1986 | Green et al. |
| 4,580,712 A | 4/1986 | Green |
| 4,585,153 A | 4/1986 | Failla et al. |
| 4,589,582 A | 5/1986 | Bilotti |
| 4,602,634 A | 7/1986 | Barkley |
| 4,605,001 A | 8/1986 | Rothfuss et al. |
| 4,605,004 A | 8/1986 | Di Giovanni et al. |
| 4,606,344 A | 8/1986 | Di Giovanni |
| 4,606,345 A | 8/1986 | Dorband et al. |
| 4,607,636 A | 8/1986 | Kula et al. |
| 4,612,933 A | 9/1986 | Brinkerhoff et al. |
| 4,617,928 A | 10/1986 | Alfranca |
| 4,632,290 A | 12/1986 | Green et al. |
| 4,665,916 A | 5/1987 | Green |
| 4,684,051 A | 8/1987 | Akopov et al. |
| 4,714,187 A | 12/1987 | Green |
| 4,715,520 A | 12/1987 | Roehr, Jr. et al. |
| 4,728,020 A | 3/1988 | Green et al. |
| 4,767,044 A | 8/1988 | Green |
| 4,788,978 A | 12/1988 | Strekopytov et al. |
| 4,802,614 A | 2/1989 | Green et al. |
| 4,805,823 A | 2/1989 | Rothfuss |
| 4,819,853 A | 4/1989 | Green |
| 4,848,637 A | 7/1989 | Pruitt |
| 4,869,414 A | 9/1989 | Green et al. |
| 4,881,544 A | 11/1989 | Green et al. |
| 4,881,545 A | 11/1989 | Isaacs et al. |
| 4,915,100 A | 4/1990 | Green |
| 4,930,503 A | 6/1990 | Pruitt |
| 4,938,408 A | 7/1990 | Bedi et al. |
| 4,941,623 A | 7/1990 | Pruitt |
| 4,951,861 A | 8/1990 | Schulze et al. |
| 4,964,559 A | 10/1990 | Deniega et al. |
| 5,005,754 A | 4/1991 | Van Overloop |
| 5,018,657 A | 5/1991 | Pedlick et al. |
| 5,071,052 A | 12/1991 | Rodak et al. |
| 5,100,042 A | 3/1992 | Gravener et al. |
| 5,116,349 A | 5/1992 | Aranyi |
| 5,137,198 A | 8/1992 | Nobis et al. |
| 5,172,845 A | 12/1992 | Tejeiro |
| 5,190,203 A | 3/1993 | Rodak |
| 5,219,111 A | 6/1993 | Bilotti et al. |
| 5,240,163 A | 8/1993 | Stein et al. |
| 5,344,060 A | 9/1994 | Gravener et al. |
| 5,368,599 A | 11/1994 | Hirsch et al. |
| 5,381,943 A * | 1/1995 | Allen ............... A61B 17/0682 |
| | | 227/177.1 |
| 5,405,073 A | 4/1995 | Porter |
| 5,413,267 A | 5/1995 | Solyntjes et al. |
| 5,439,155 A | 8/1995 | Viola |
| 5,452,836 A | 9/1995 | Huitema et al. |
| 5,458,279 A | 10/1995 | Plyley |
| 5,462,215 A | 10/1995 | Viola et al. |
| 5,464,144 A | 11/1995 | Guy et al. |
| 5,465,894 A | 11/1995 | Clark et al. |
| 5,470,006 A | 11/1995 | Rodak |
| 5,470,008 A | 11/1995 | Rodak |
| 5,470,009 A | 11/1995 | Rodak |
| 5,484,451 A | 1/1996 | Akopov et al. |
| 5,497,934 A | 3/1996 | Brady et al. |
| 5,503,320 A | 4/1996 | Webster et al. |
| 5,509,596 A | 4/1996 | Green et al. |
| 5,542,594 A | 8/1996 | McKean et al. |
| 5,547,117 A | 8/1996 | Hamblin et al. |
| 5,558,266 A | 9/1996 | Green et al. |
| 5,579,978 A | 12/1996 | Green et al. |
| 5,580,067 A | 12/1996 | Hamblin et al. |
| 5,603,443 A | 2/1997 | Clark et al. |
| 5,605,272 A | 2/1997 | Witt et al. |
| 5,605,273 A | 2/1997 | Hamblin et al. |
| 5,607,094 A | 3/1997 | Clark et al. |
| 5,615,820 A | 4/1997 | Viola |
| 5,641,111 A | 6/1997 | Ahrens et al. |
| 5,678,748 A | 10/1997 | Plyley et al. |
| 5,697,543 A | 12/1997 | Burdorff |
| 5,706,997 A | 1/1998 | Green et al. |
| 5,706,998 A | 1/1998 | Plyley et al. |
| 5,732,871 A | 3/1998 | Clark et al. |
| 5,735,445 A | 4/1998 | Vidal et al. |
| 5,794,834 A | 8/1998 | Hamblin et al. |
| 5,810,240 A | 9/1998 | Robertson |
| 5,855,311 A | 1/1999 | Hamblin et al. |
| 5,878,937 A | 3/1999 | Green et al. |
| 5,893,506 A | 4/1999 | Powell |
| 5,894,979 A | 4/1999 | Powell |
| 5,964,394 A | 10/1999 | Robertson |
| 6,045,560 A | 4/2000 | McKean et al. |
| 6,638,285 B2 | 10/2003 | Gabbay |
| 6,805,273 B2 | 10/2004 | Bilotti et al. |
| 6,817,508 B1 | 11/2004 | Racenet et al. |
| 6,988,650 B2 | 1/2006 | Schwemberger et al. |
| 7,070,083 B2 | 7/2006 | Jankowski |
| 7,134,587 B2 | 11/2006 | Schwemberger et al. |
| 7,147,139 B2 | 12/2006 | Schwemberger et al. |
| 7,147,140 B2 | 12/2006 | Wukusick et al. |
| 7,204,404 B2 | 4/2007 | Nguyen et al. |
| 7,207,472 B2 | 4/2007 | Wukusick et al. |
| 7,210,609 B2 | 5/2007 | Leiboff et |
| 7,237,708 B1 | 7/2007 | Guy et al. |
| 7,275,674 B2 | 10/2007 | Racenet et al. |
| RE40,237 E | 4/2008 | Bilotti et al. |
| 7,407,076 B2 | 8/2008 | Racenet et al. |
| 7,431,190 B2 | 10/2008 | Hoffman |
| 7,522,854 B2 | 4/2009 | Kinouchi et al. |
| 7,549,563 B2 | 6/2009 | Mather et al. |
| 7,556,185 B2 | 7/2009 | Viola |
| 7,568,605 B2 | 8/2009 | Kruszynski |
| 7,641,092 B2 | 1/2010 | Kruszynski et al. |
| 7,641,671 B2 * | 1/2010 | Crainich ............... A61B 17/12 |
| | | 606/151 |
| 7,717,312 B2 | 5/2010 | Beetel |
| 7,731,073 B2 | 6/2010 | Wixey et al. |
| 7,735,704 B2 | 6/2010 | Bilotti |
| 7,766,207 B2 | 8/2010 | Mather et al. |
| 7,798,386 B2 * | 9/2010 | Schall ............ A61B 17/07207 |
| | | 227/175.1 |
| 7,810,690 B2 | 10/2010 | Bilotti et al. |
| 7,914,543 B2 * | 3/2011 | Roth ................. A61F 5/0083 |
| | | 227/175.1 |

(56) References Cited

U.S. PATENT DOCUMENTS

| | | |
|---|---|---|
| 8,016,176 B2 | 9/2011 | Kasvikis et al. |
| 8,033,439 B2 | 10/2011 | Racenet et al. |
| 8,231,041 B2 | 7/2012 | Marczyk et al. |
| 8,393,514 B2 | 3/2013 | Shelton, IV et al. |
| 8,424,738 B2 | 4/2013 | Kasvikis |
| 8,499,994 B2 | 8/2013 | D'Arcangelo |
| 8,556,151 B2 | 10/2013 | Viola |
| 8,568,443 B1 | 10/2013 | Jackman et al. |
| 8,757,467 B2 | 6/2014 | Racenet et al. |
| 8,789,737 B2 | 7/2014 | Hodgkinson et al. |
| 8,858,571 B2 * | 10/2014 | Shelton, IV ..... A61B 17/07207 227/175.1 |
| 8,926,598 B2 * | 1/2015 | Mollere ........... A61B 17/07207 227/175.1 |
| 9,113,879 B2 * | 8/2015 | Felder ................. A61B 17/072 |
| 9,125,662 B2 * | 9/2015 | Shelton, IV ....... A61B 18/1445 |
| 9,585,657 B2 * | 3/2017 | Shelton, IV ..... A61B 17/07207 |
| 2003/0036748 A1 | 2/2003 | Cooper ............ A61B 17/00234 606/1 |
| 2004/0164123 A1 | 8/2004 | Racenet et al. |
| 2005/0006432 A1 * | 1/2005 | Racenet ........... A61B 17/07207 227/176.1 |
| 2005/0165429 A1 * | 7/2005 | Douglas ................. A61B 17/08 606/157 |
| 2005/0247752 A1 | 11/2005 | Kelly et al. |
| 2005/0247753 A1 | 11/2005 | Kelly et al. |
| 2006/0151568 A1 * | 7/2006 | Weller ............... A61B 17/0218 227/175.1 |
| 2006/0163312 A1 | 7/2006 | Viola et al. |
| 2007/0175949 A1 * | 8/2007 | Shelton ............ A61B 17/07207 227/176.1 |
| 2007/0187456 A1 | 8/2007 | Viola et al. |
| 2008/0308607 A1 * | 12/2008 | Timm .............. A61B 17/07207 227/176.1 |
| 2009/0182354 A1 * | 7/2009 | Blier ...................... A61B 17/04 606/148 |
| 2009/0277948 A1 | 11/2009 | Beardsley et al. |
| 2010/0048988 A1 | 2/2010 | Pastorelli et al. |
| 2011/0295295 A1 * | 12/2011 | Shelton, IV ......... A61B 17/072 606/170 |
| 2012/0253329 A1 | 10/2012 | Zemlok et al. |
| 2013/0098966 A1 | 4/2013 | Kostrzewski et al. |
| 2013/0105554 A1 | 5/2013 | Kostrzewski |
| 2016/0081690 A1 * | 3/2016 | Baxter, III ........... A61B 17/068 227/180.1 |
| 2016/0174977 A1 * | 6/2016 | Lytle, IV ......... A61B 17/07207 227/180.1 |
| 2016/0174978 A1 * | 6/2016 | Overmyer ........ A61B 17/07207 227/178.1 |
| 2016/0174983 A1 * | 6/2016 | Shelton, IV ......... A61B 17/068 227/176.1 |

FOREIGN PATENT DOCUMENTS

| | | |
|---|---|---|
| WO | 2008056618 A2 | 5/2008 |
| WO | 2013009699 A2 | 1/2013 |
| WO | 2014030110 A1 | 2/2014 |

OTHER PUBLICATIONS

U.S. Appl. No. 14/590,059, filed Jan. 6, 2015, inventor: Kostrzewski.

\* cited by examiner

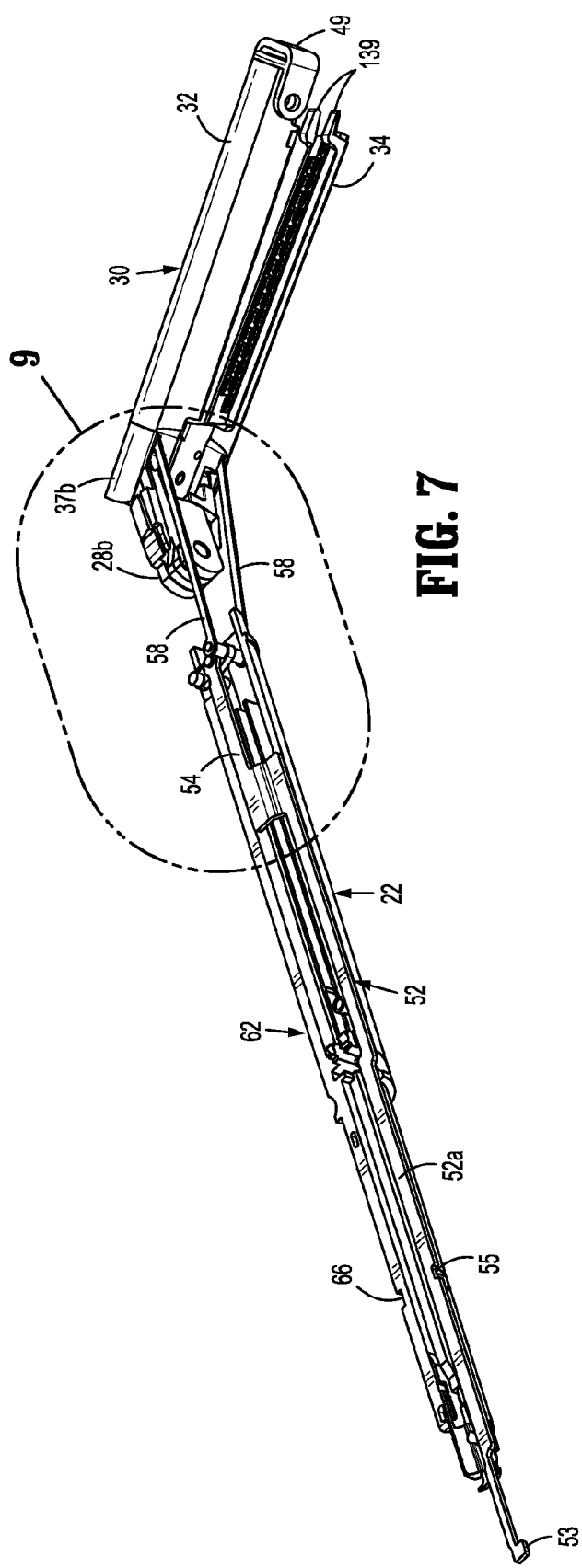
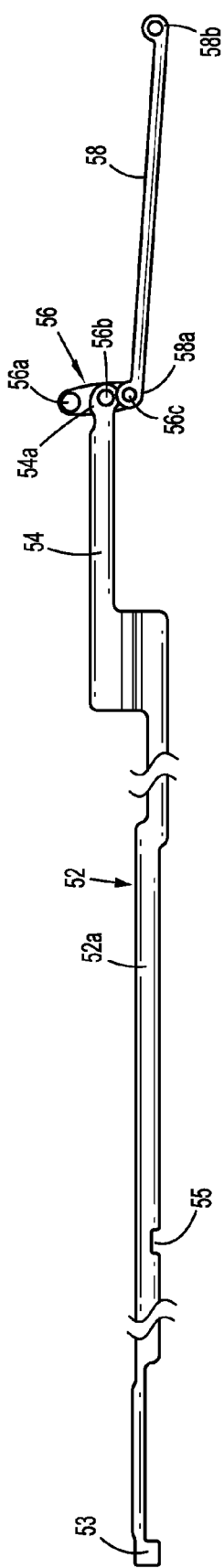
FIG. 7
FIG. 8

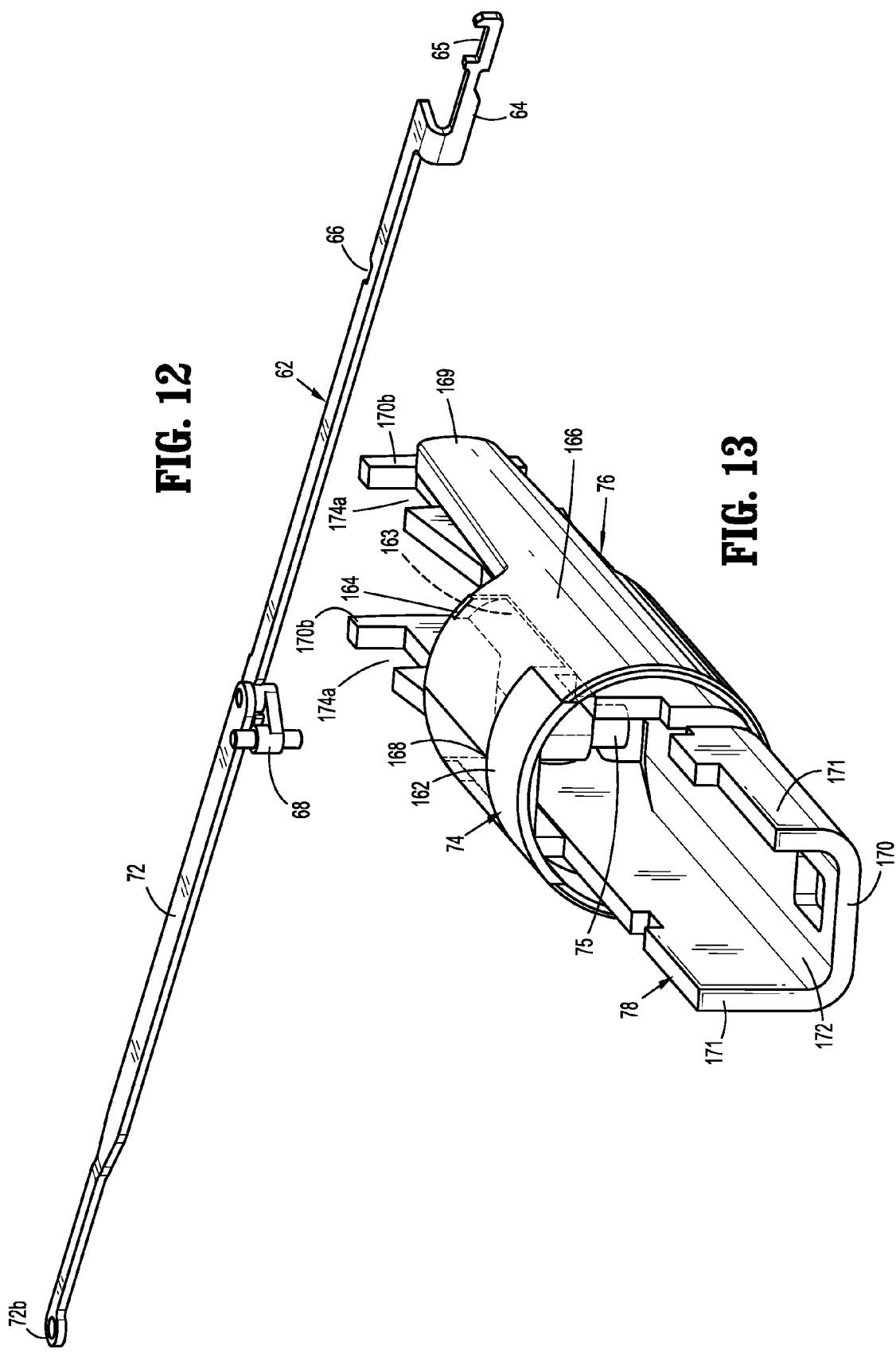

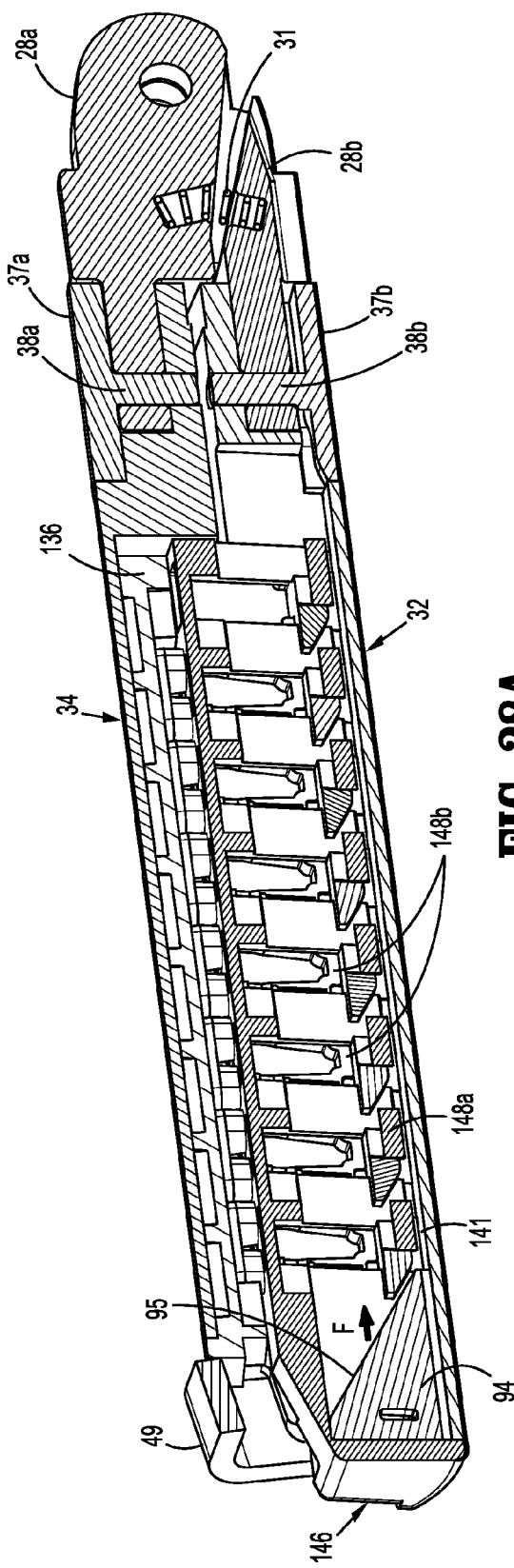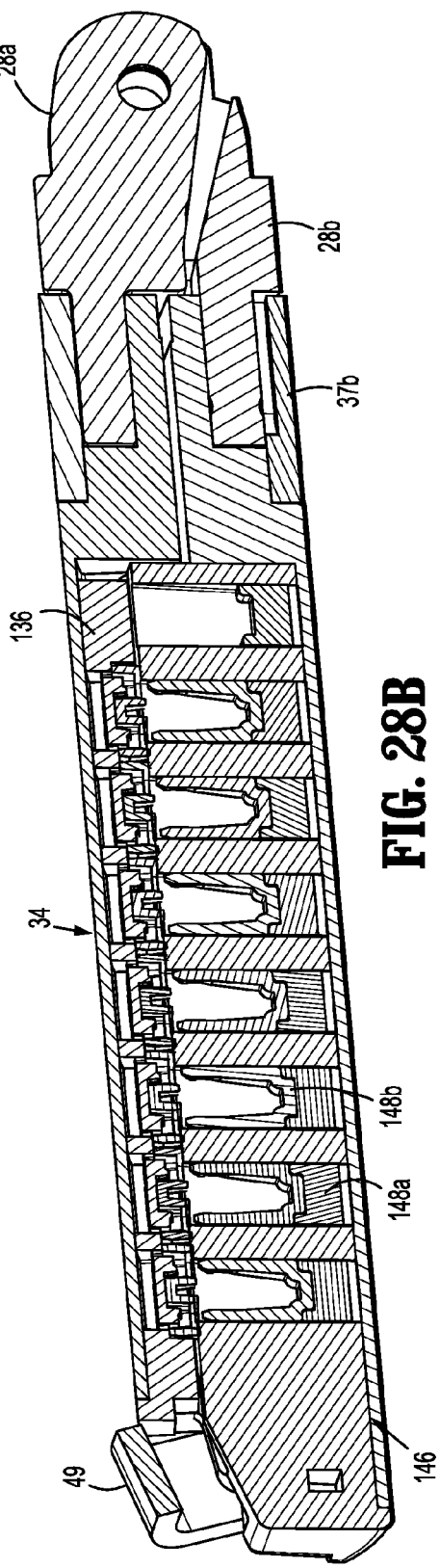
FIG. 28A
FIG. 28B

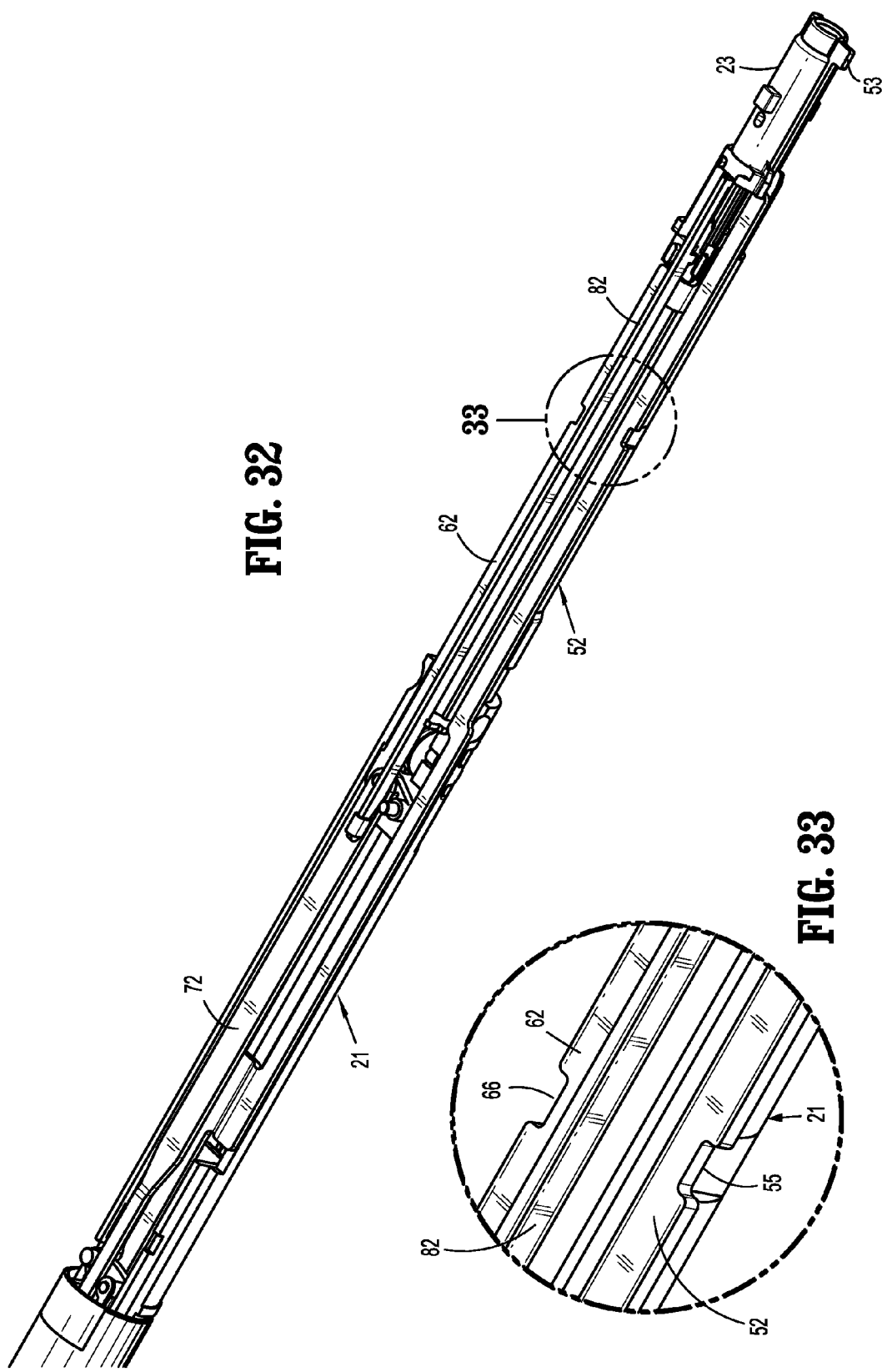

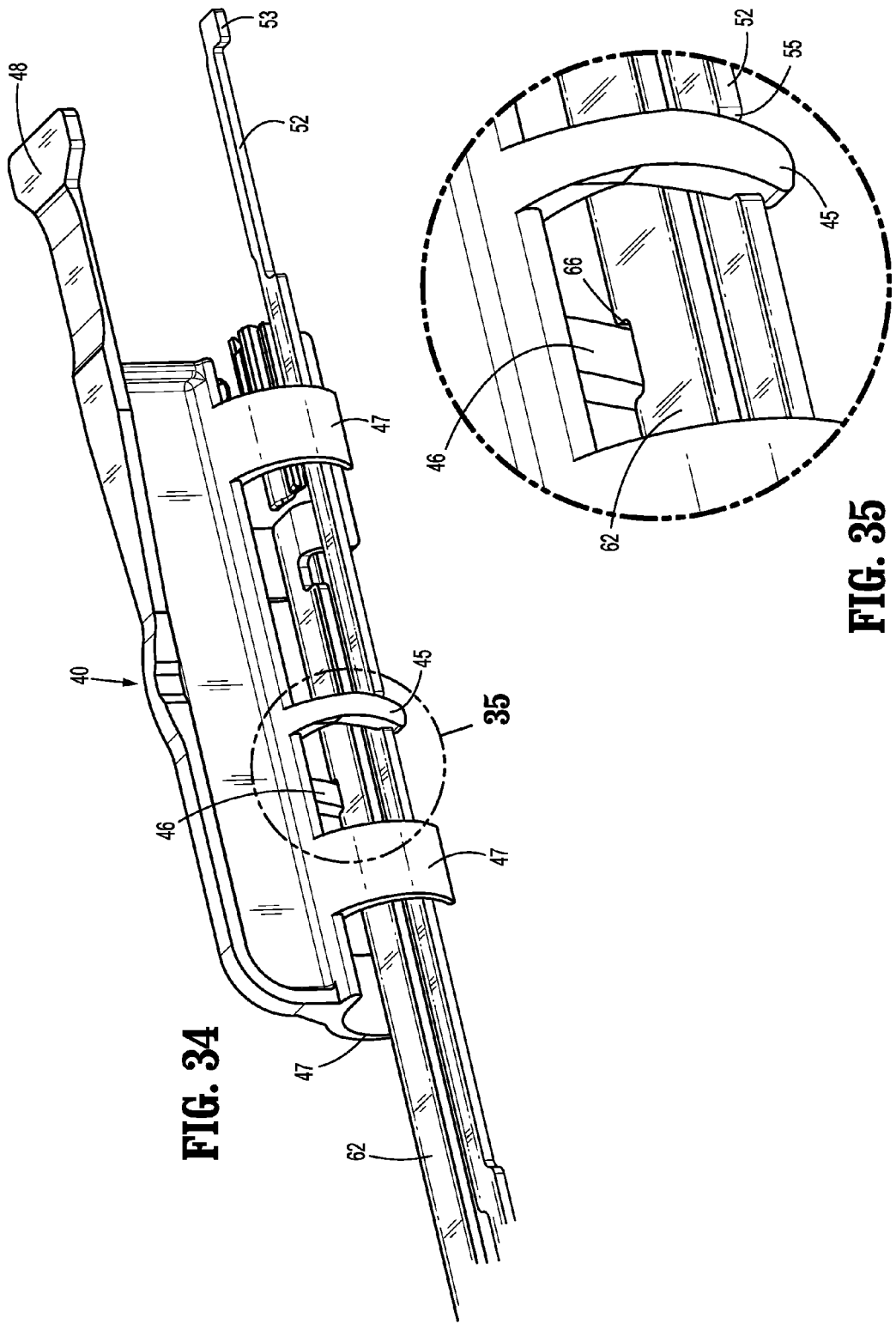

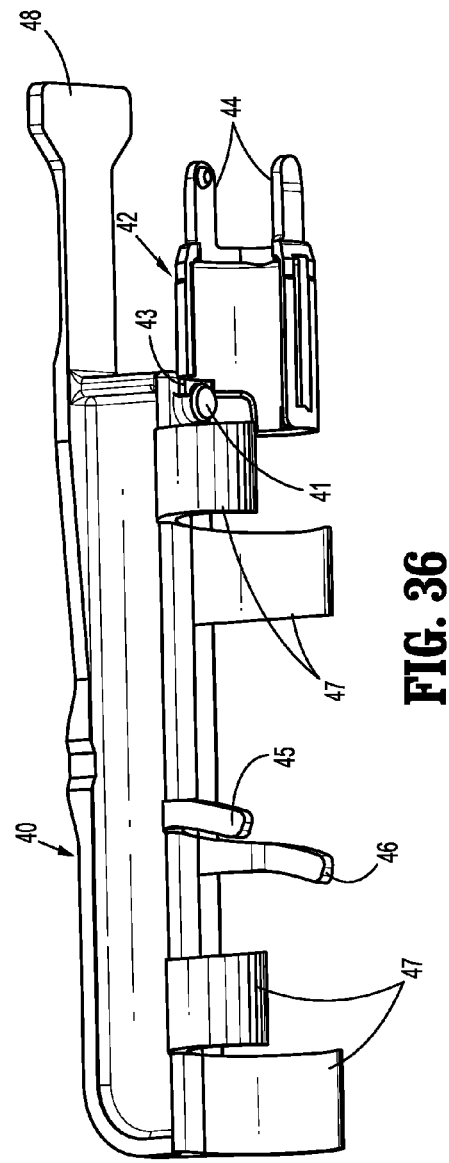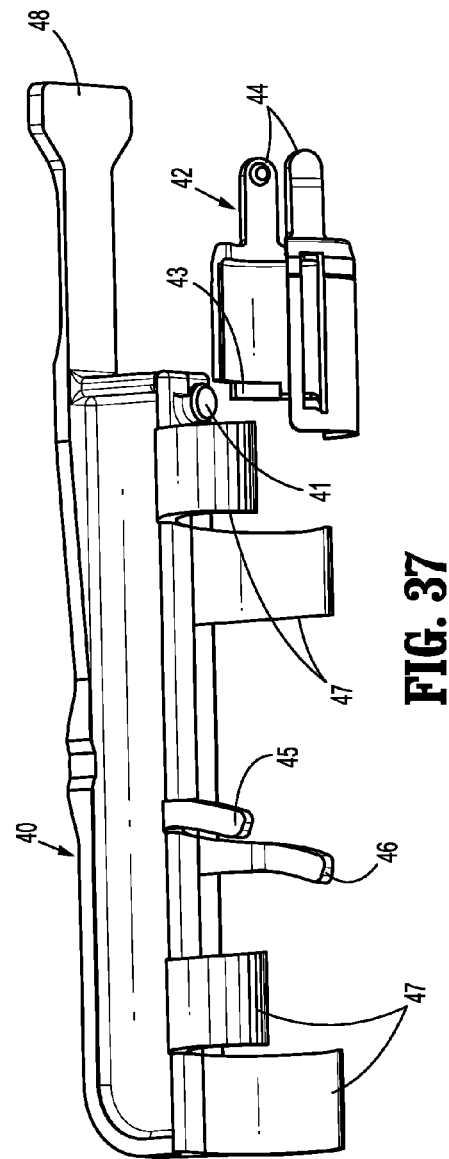

SURGICAL STAPLING LOADING UNIT HAVING ARTICULATING JAWS

BACKGROUND

1. Technical Field

The present disclosure relates to surgical instruments and, more specifically, to surgical stapling loading units having articulating jaws.

2. Discussion of Related Art

During hysterectomy procedures, such as total laparoscopic hysterectomy (TLH) procedures, the uterus and cervix are removed, creating an approximately circular structure at end of the vaginal canal called the vaginal cuff. The closure of the remaining vaginal cuff can be one of the most challenging aspects of the procedure. It is also considered to be one of the barriers to adoption of laparoscopic surgery to those trained in open procedures.

After the uterus is removed it is necessary to close the vaginal cuff while avoiding dehiscence, which is when a wound ruptures along a surgical suture. Currently the vaginal cuff closure is done manually by suturing the cuff with needle and suture or with a stitching surgical instrument. Both methods require surgical skill and time. Suturing may also yield inconsistent results due to varying skills among surgeons.

Some loading units for surgical instruments include an elongated body and end effector that is articulatable relative to the elongated body. Typically, these loading units have jaws that pivot between open and closed positions such that the jaws close in a non-parallel manner. Other loading units include jaws that close in a parallel manner.

There is a need for a loading unit with an end effector including jaws that are articulatable relative to an elongated body with jaws that close in a parallel manner. In addition, there is a need for a loading unit that can close a vaginal cuff which requires less skill, saves time, and provides strong, consistent anastomosis.

SUMMARY

In an aspect of the present disclosure, an end effector includes a first jaw member, a second jaw member, and a pivot pin. The first jaw member includes a first camming member, a first body, and a first coupling member. The first camming member defines a first rotation hole and a first pivot hole. The first body has a first proximal tab that defines a first rotation opening and a first articulation opening. The first coupling member has a first rotation post and a first articulation post. The first rotation post is inserted in the first rotation hole and the first rotation opening. The first articulation post is positioned within the first articulation opening. The second jaw member includes a second camming member, a second body, and a second coupling member. The second camming member defines a second rotation hole and a second pivot hole. The second body has a second proximal tab that defines a second rotation opening and a second articulation opening. The second coupling member has a second rotation post and a second articulation post. The second rotation post is inserted in the second rotation hole and the second rotation opening. The second articulation post is positioned within the second articulation opening. The pivot pin is positioned in the first and second pivot holes such that the first and second jaw members are pivotable relative to one another in a substantially parallel manner between open and clamped configurations about the pivot pin. The first and second bodies are also articulatable relative to the first and second camming members about the first and second articulation posts.

In aspects, the first and second rotation holes are distal of the first and second pivot holes. The first and second rotation holes may be orthogonal to the first and second pivot holes.

In some aspects, the first camming member includes first sidewalls and the second camming member includes second sidewalls. The first sidewalls may define the first pivot hole and the second sidewalls may define the second pivot hole. The second sidewalls may define a channel and the first sidewalls may be inserted in the channel to axially align the first and second pivot holes. The first camming member may include a first support arm that extends distally from the first sidewalls which defines the first rotation hole. The second camming member may include a second support arm that extends distally from the second sidewalls which defines the second rotation hole.

In certain aspects, the first body includes a distally extending locking finger and the second body includes a locking member that is rotatably coupled to a distal end of the second body. The locking member may be rotatable over the locking finger when the first and second jaw members are in the clamped configuration to maintain the first and second members in the clamped configuration.

In particular aspects, the first and second bodies are articulatable between a straight configuration and a fully articulated configuration. The first and second bodies may be longitudinally aligned with the first and second camming members in the straight configuration and may define an angle with the first and second camming members in the fully articulated configuration. The fully articulated configuration may be defined by the first and second bodies being articulated in a range of 75° to 105° from the first and second camming members.

In another aspect of the present disclosure, a loading unit includes an end effector and a housing. The end effector includes a first jaw member, a second jaw member, and a pivot pin. The first jaw member includes a first camming member, a first body, and a first coupling member. The first camming member defines a first rotation hole and a first pivot hole. The first rotation hole is orthogonal to and distal of the first pivot hole. The first body has a first proximal tab that defines a first rotation opening and a first articulation opening. The first coupling member has a first rotation post and a first articulation post. The first rotation post is inserted in the first rotation hole and the first rotation opening. The first articulation post is positioned within the first articulation opening. The second jaw member includes a second camming member, a second body, and a second coupling member. The second camming member defines a second rotation hole and a second pivot hole. The second rotation hole is orthogonal to and distal of the second pivot hole. The second body has a second proximal tab that defines a second rotation opening and a second articulation opening. The second coupling member has a second rotation post and a second articulation post. The second rotation post is inserted in the second rotation hole and the second rotation opening. The second articulation post is positioned within the second articulation opening. The pivot pin is positioned in the first and second pivot holes. The housing includes a connector, a clamping mechanism, and an articulation mechanism. The connector is positioned at a proximal end of the housing and is configured to couple the loading unit to a surgical instrument. The housing also defines a longitudinal axis of the loading unit. The clamping mechanism is operatively associated with the first and second camming members to pivot the first and second jaw members relative to one another about the pivot pin between open configuration and clamped configurations. The articulation mechanism is operatively associated with the first and second coupling member to articulate the first and second bodies about the first and second articulation posts between straight and fully articulated configurations.

In aspects, the articulation mechanism includes first and second articulation rods. A distal end of the first articulation rod is coupled to the first articulation post and a distal end of the second articulation rod is coupled to the second articulation post. The articulation mechanism may include an articulation pivot arm that has first, second, and third pivots. The first pivot may be positioned at a first end of the articulation pivot arm and may be rotatably supported within the housing. The third pivot may be positioned at a second end of the articulation pivot arm and may be coupled to proximal ends of the first and second articulation rods. The second pivot may be positioned between the first and second ends of the articulation pivot arm. The articulation mechanism may include an articulation shaft that has a distal end coupled to the second pivot and a proximal end positioned adjacent the connector of the housing. The first and second bodies may be adapted to articulate between the straight and articulated configurations in response to longitudinal translation of the articulation shaft. The articulation shaft may have a proximal flag that is adjacent the connector of the housing. The proximal flag may be configured to be engaged by the surgical instrument to translate the articulation shaft longitudinally.

In some aspects, the clamping mechanism moves the first and second bodies towards the clamped configuration in a substantially parallel manner when the first and second jaw members are in the fully articulated configuration. The first and second camming members may each include a camming surface. The clamping mechanism may include a clamping sleeve that has a distal end. The clamping sleeve may be positioned about the first and second camming members and be longitudinally translatable between proximal and distal position. The clamping sleeve may engage the clamping surfaces of the first and second camming members as the clamping sleeve is translated towards the distal position to pivot the first and second jaw members towards the clamped position. The first and second camming members may each include a clamp stop at a distal end of the camming surfaces. The clamping sleeve may abut the clamp stop when the clamping sleeve is in the distal position. The clamp stops may be positioned proximal to the first and second pivot holes, the first and second rotation posts, or the pivot pin. Portions of the camming surfaces of the first and second camming members may extend proximally of the first and second pivot holes, the first and second rotation posts, or the pivot pin In certain aspects, the clamping mechanism includes a clamping pivot arm, a clamping rod, and a clamping shaft. The clamping pivot arm may have a first end that is rotatably supported within the housing, a second end, and a cam follower positioned between the first and second ends. The cam follower may be a body connecting the first and second ends. The clamping rod may have a distal end that is operatively coupled to the clamping sleeve and a proximal end that is coupled to the second end of the clamping pivot arm. The clamping shaft may have a clamping hook that is positioned at a distal end of the clamping shaft. The clamping hook may engage the cam follower of the clamping pivot arm to rotate the clamping pivot arm about its first end to move the clamping sleeve between the proximal and distal position in response to longitudinal translation of the clamping shaft. The clamping shaft may have a proximal end that is positioned adjacent the connector of the housing and is configured to be engaged by the surgical instrument. The proximal end may define a notch that receives a carriage.

In particular aspects, the second jaw member includes a fastener cartridge that has a plurality of fasteners. The housing may include a firing mechanism that is operatively associated with the second jaw member to eject the plurality of fasteners from the fastener cartridge towards the first jaw member. The firing mechanism may include a firing rod and a firing cable. The firing rod may be longitudinally translatable within the housing and have a proximal and distal ends. The proximal end of the firing rod may be positioned adjacent the connector of the housing and may be configured to be engaged by the surgical instrument. The proximal end of the firing rod may engage the carriage to translate the firing rod longitudinally within the housing. The firing cable may have one end that is coupled to the distal end of the firing rod and another end that is coupled to a sled which is positioned in the second jaw member. The firing cable may pull the sled through the second jaw member to eject the plurality of fasteners from the fastener cartridge in response to longitudinal translation of the firing rod. The firing cable may extend proximally from the distal end of the firing rod, around a firing pulley, and through the second jaw member to couple to the sled such that distal translation of the firing rod pulls the sled proximally through the second jaw member. A lower surface of the second camming member and an upper surface of the second coupling member may each define a portion of a firing cable groove that slidingly receives a portion of the firing cable between the sled and the distal end of the firing rod.

In aspects, the loading unit includes a shipping lock which secures the first and second jaw members in a shipping configuration such that the end effector is between the straight and fully articulated configurations and the second first and second jaw members are between the open and clamped configurations. The shipping lock may be positioned on the housing and include an articulation finger and a clamping finger. The articulation finger may be engaged with the articulation mechanism to prevent articulation of the first and second bodies from the shipping configuration. The clamping finger may engage the clamping mechanism to prevent the clamping mechanism from moving towards a proximal position to secure the first and second jaw members in the shipping configurations. The shipping configuration may be defined by the clamping sleeve of the clamping mechanism being engaged with the camming surfaces of each of the first and second camming members to prevent the first and second jaw members from moving towards the open configuration.

In some aspects, the housing includes a jaw support that is supported in and extends from the distal end of the housing. The jaw support may have sidewalls that define a channel therebetween. Each of the sidewalls may define a pivot pin opening that supports the pivot pin. The first and second camming members may be positioned within the channel between the sidewalls of the jaw support with the pivot holes of the first and second camming members axially aligned with the pivot pin openings. The sidewalls of the jaw support may prevent the first and second bodies from articulating when the first and second jaw members are in the clamped configuration. A distal portion of each of the sidewalls of the jaw support may define an upper clamping pocket that may receive the first body when the end effector is in the fully articulated and clamped configurations. The distal portion of each of the sidewalls of the jaw support may define a lower clamping pocket which receives the second body when the end effector is in the fully articulated configuration and the clamped configuration. The sidewalls of the jaw support may maintain the first and second jaw members spaced apart from one another when the first and second bodies are articulated between the straight and fully articulated positions. In the shipping configuration of the end effector, the clamping mechanism may engage the first and second camming members to move the first and second bodies into engagement with the sidewalls of the jaw support to maintain the first and second bodies spaced apart from one another.

In another aspect of the present disclosure, a jaw member of an end effector includes a camming member, a body, and a coupling member. The camming member defines a rotation hole and a pivot hole. The rotation hole is orthogonal to and distal of the pivot hole. The body has a proximal tab that defines a rotation opening and an articulation opening. The coupling member has a rotation post and an articulation post. The rotation post is inserted in the rotation hole and the rotation opening. The articulation post is positioned within the articulation opening. The jaw member is configured to pivot about the pivot hole and the body is configured to articulate relative to the camming member about the rotation post.

In aspects, the camming member includes sidewalls and a support arm that extends distally from the sidewalls. The sidewalls may define the pivot hole and the support arm may define the rotation hole.

In another aspect of the present disclosure, an end effector includes first and second jaw members that are pivotable relative to one another between open and clamped configurations about a pivot axis. The first and second jaw members each define a pivot hole which defines the pivot axis. The first and second jaw members also each define an articulation axis that is orthogonal to the pivot axis and positioned distal of the pivot axis. The first and second jaw members are articulatable about the articulation axis between straight and fully articulated configurations.

In aspects, in the fully articulated configuration the first and second jaw members are configured to pivot in a substantially parallel manner between the open and clamped configurations.

In another aspect of the present disclosure, a method for closing a vaginal cuff includes inserting a loading unit through an opening with first and second jaw members of an end effector of the loading unit in a straight configuration, articulating a portion of each of first and second jaw members, pivoting the first and second jaw members to a clamped configuration, and ejecting a plurality of fasteners. In the straight configuration of the first and second jaw members, the first and second jaw members are aligned with a longitudinal axis of the loading unit. Articulating the portion of each of the first and second jaw members includes articulating the portion of the first and second jaw members relative to another portion of the first and second jaw members such that the portion of the first and second jaw members are perpendicular to a vaginal cuff of a patient. Pivoting the first and second jaw members to the clamped configuration includes pivoting the first and second jaw members about a pivot axis passing through unarticulated portions of each of the first and second jaw members such that the articulated portions of each of the first and second jaw members clamp onto the vaginal cuff of the patient in a substantially parallel manner. The plurality of fasteners are ejected from the articulated portion of the first jaw member towards the articulated portion of the second jaw member to close the vaginal cuff.

Further, to the extent consistent, any of the aspects described herein may be used in conjunction with any or all of the other aspects described herein.

BRIEF DESCRIPTION OF THE DRAWINGS

Various aspects of the present disclosure are described hereinbelow with reference to the drawings, which are incorporated in and constitute a part of this specification, wherein:

FIG. 7 is a lower perspective view of the loading unit of FIG. 1 with the lower housing portion and portions of the clamping assembly removed;

FIG. 8 is a bottom view of the articulating mechanism of FIG. 7;

FIG. 12 is a perspective view of a portion of the clamping mechanism of FIG. 2 which is disposed within the housing, with the housing removed;

FIG. 13 is a rear perspective view of a portion of the clamping mechanism of FIG. 2 which is supported at a distal end of the housing;

FIG. 28A is cross-sectional view taken along the section line 28A-28A of FIG. 3 with a sled in an initial position;

FIG. 28B is cross-sectional view taken along the section line 28B-28B of FIG. 3 with fasteners disposed within the fastener cartridge;

FIG. 32 is a perspective view of the loading unit of FIG. 1 in a shipping configuration with the upper housing portion removed;

FIG. 33 is an enlarged view of the indicated area of detail of FIG. 32;

FIG. 34 is a perspective view of a proximal portion of the loading unit of FIG. 32 with the lower housing portion removed and including the shipping lock of FIG. 1;

FIG. 35 is an enlarged view of the indicated area of detail of FIG. 34;

FIG. 36 is a perspective view of the shipping lock and locking ring of FIG. 2;

FIG. 37 is a perspective view of the shipping lock and the locking ring of FIG. 36 with the locking ring rotated to an unlocked position;

DETAILED DESCRIPTION

Figure 1:
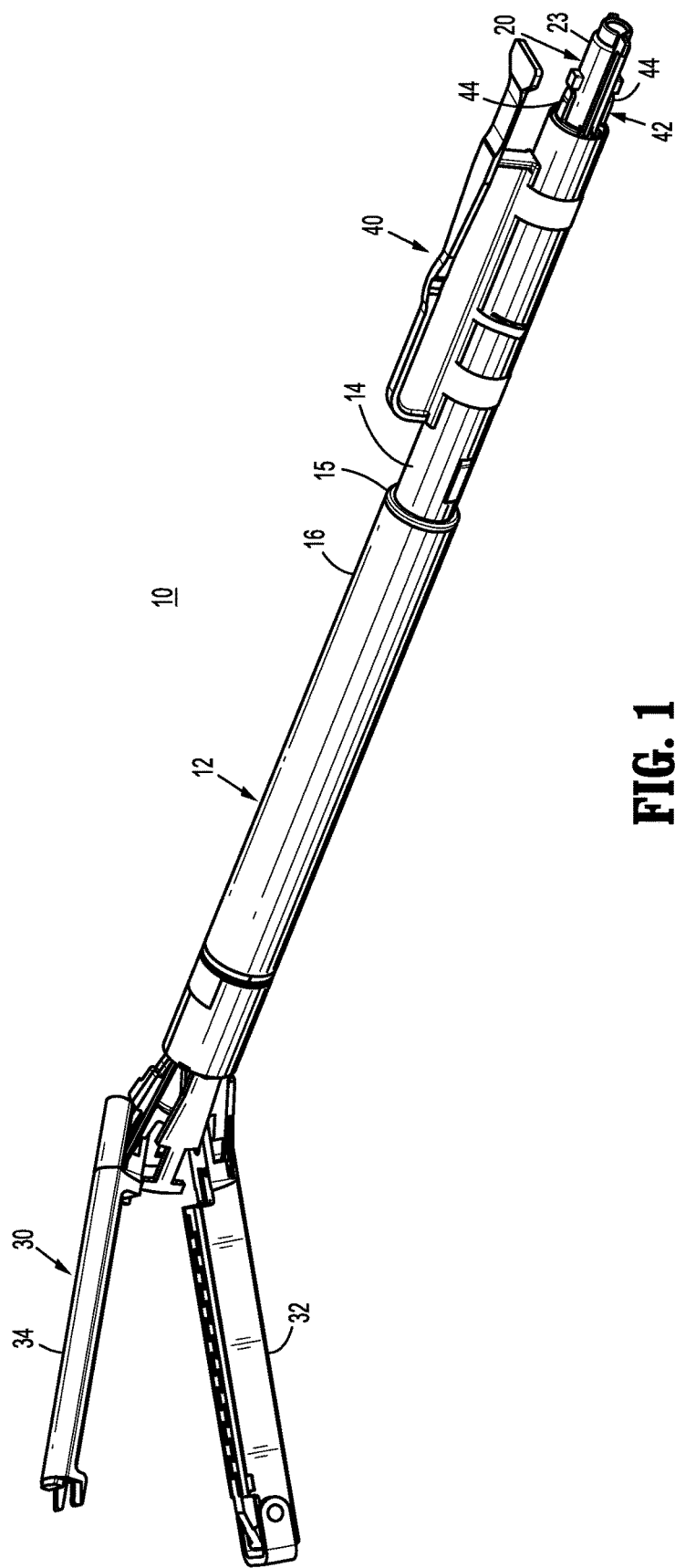
FIG. 1 is a perspective view of a loading unit provided in accordance with the present disclosure in a shipping configuration.

Embodiments of the present disclosure are now described in detail with reference to the drawings in which like reference numerals designate identical or corresponding elements in each of the several views. As used herein, the term "clinician" refers to a doctor, a nurse, or any other care provider and may include support personnel. Throughout this description, the term "proximal" refers to the portion of the device or component thereof that is closest to the clinician and the term "distal" refers to the portion of the device or component thereof that is farthest from the clinician.

This disclosure relates generally to a loading unit for a powered or manual surgical handle, or for use with a robotic surgical system, including an articulatable end effector for joining tissue with a substantially parallel closure. The end effector is articulatable relative to an elongated body of the loading unit and includes a retainer jaw and a fastener jaw that are moveable relative to one another. As described in greater detail below, during a procedure, the loading unit is inserted through an incision in a straight configuration with the entire end effector aligned with the elongated body. Portions of the end effector are then articulated to an articulated configuration such that the portions of the end effector are articulated from a longitudinal axis of the elongated body with the retainer and fastener jaws in an open configuration. The articulated portions of the fastener and retainer jaws are then moved in a substantially parallel manner towards a clamped configuration over an end of a vaginal cuff. Fasteners disposed within the fastener jaw are then fired through the vaginal cuff to close the vaginal cuff. Alternatively, the presently disclosed loading unit is useable in other minimally invasive procedures (e.g., laparoscopic, endoscopic, etc.).

Referring now to FIG. 1, the loading unit 10 is provided in accordance with the present disclosure and includes an elongated body 12 extending from a connector 23 to an end effector 30. As shown in FIG. 1 and described in greater detail below, the loading unit 10 is in a shipping configuration with a shipping lock 40 secured about a proximal tube 14 of the elongated body 12. The connector 23 is configured to couple the loading unit 10 to a surgical instrument (not shown) including a drive rod which actuates the loading unit 10 to articulate the end effector 30 relative to the elongated body 12, to clamp tissue within the end effector 30, and to form fasteners 148b (FIG. 43) through the clamped tissue.

The connector 23 of the loading unit 10 may be configured for selective connection to a powered hand held electromechanical instrument (not shown), may be configured for selective connection to an adapter for a powered or manual instrument (not shown), or may be configured for selective connection to a manually actuated handle assembly (not shown). For a detailed description of the structure and function of an exemplary manually actuated handle assembly, please refer to commonly owned U.S. Pat. No. 8,789,737, the entire disclosure of which is hereby incorporated by reference herein. For a detailed description of the structure and function of an exemplary electromechanical instrument and adapter, please refer to commonly owned U.S. patent application Ser. No. 13/484,975, filed on May 31, 2012, now published as U.S. Patent Publication No. 2012/0253329, each of these disclosures is incorporated herein by reference in its entirety.

Figure 2:
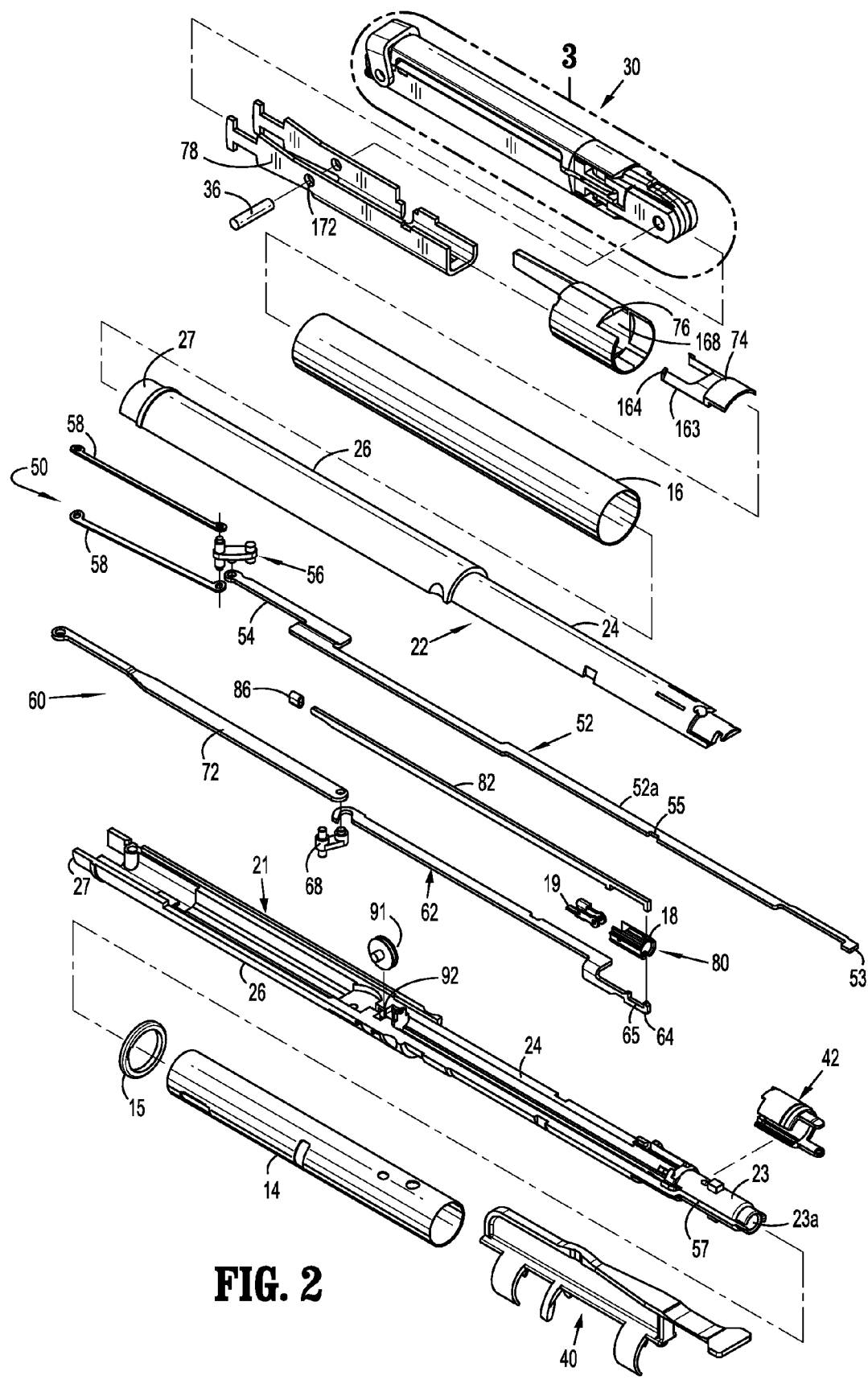
FIG. 2 is an exploded view, with parts separated, illustrating the internal components of the loading unit of FIG. 1.

With additional reference to FIG. 2, the elongated body 12 includes an inner housing 20 (FIG. 1) formed from a lower housing portion 21 and an upper housing portion 22. The inner housing 20 includes the connector 23, a proximal cylinder 24, and a distal cylinder 26. The proximal cylinder 24 extends from the connector 23 and the distal cylinder 26 extends from the proximal cylinder 24. The distal cylinder 26 has a diameter that is larger than a diameter of the proximal cylinder 24. A distal extension 27 extends from the distal cylinder 26 and supports portions of a clamping mechanism 60 as detailed below. The lower housing portion 21 and the upper housing portion 22 are secured together by a proximal tube 14 disposed over the proximal cylinder 24 and a distal tube 16 disposed over the distal cylinder 26. The proximal tube 14 has a first diameter and the distal tube 16 has a second diameter that is larger than the first diameter. The first diameter may be in a range of about 5 mm to about 15 mm (e.g., 12 mm) and the second diameter may be in a range of about 12 mm to about 20 mm (e.g., 15 mm). The proximal tube 14 and the distal tube 16 may be joined by a housing ring 15 disposed over the proximal tube 14 and within the distal tube 16 as shown in FIG. 1. The housing ring 15 may seal a gap defined between the proximal and distal tubes 14, 16. As shown in FIG. 1, the connector 23 extends proximally from proximal tube 14.

Referring to FIGS. 3-6, the end effector 30 includes an upper cam member 28a, a lower cam member 28b, a fastener jaw 32, a retainer jaw 34, an upper coupling member 37a, and a lower coupling member 37b. The upper cam member 28a, retainer jaw 34 and upper coupling member 37a form a first jaw member of the end effector 30 and the lower cam member 28b, the fastener jaw 32, and the lower coupling member 37b form a second jaw member of the end effector 30. The upper and lower cam members 28a, 28b are pivotally coupled together and are moveable relative to one another to move the fastener and retainer jaws 32, 34 between an open configuration and a clamped configuration. As detailed below, the fastener jaw 32 is rotatably coupled to the lower cam member 28b and the retainer jaw 34 is rotatably coupled to the upper cam member 28a.

Figure 5:
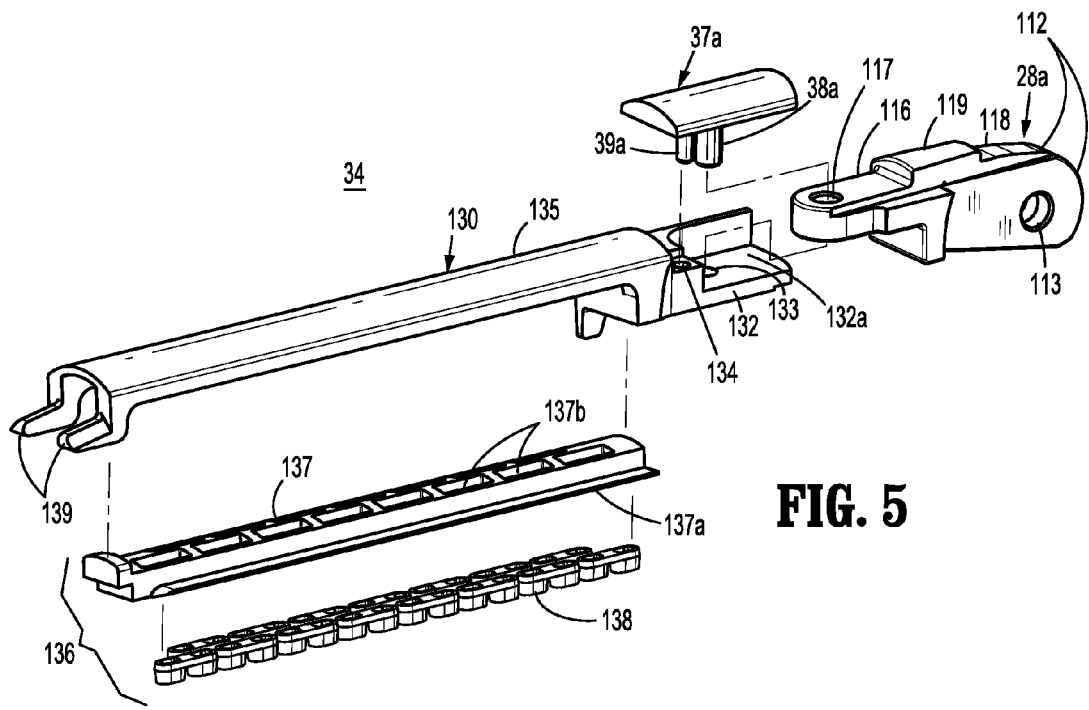
FIG. 5 is an exploded view, with parts separated, of the retainer jaw of FIG. 4.

With particular reference to FIG. 5, the upper cam member 28a includes sidewalls 112, a support arm 116, a camming surface 118, and a clamp stop 119. The sidewalls 112 each define a pivot hole 113 that is transverse to a longitudinal axis of the housing 20 (FIG. 1). The support arm 116 extends distally from the sidewalls 112 and defines a rotation hole 117. The camming surface 118 and the clamp stop 119 are disposed on an upper surface of the sidewalls 112. The clamp stop 119 is positioned at a distal end of the camming surface 118 and extends above the camming surface 118. As shown the clamp stop 119 is positioned distal of the pivot hole 113; however, it is contemplated that the clamp stop 119 may be positioned proximal of the pivot hole 113.

Figure 6:
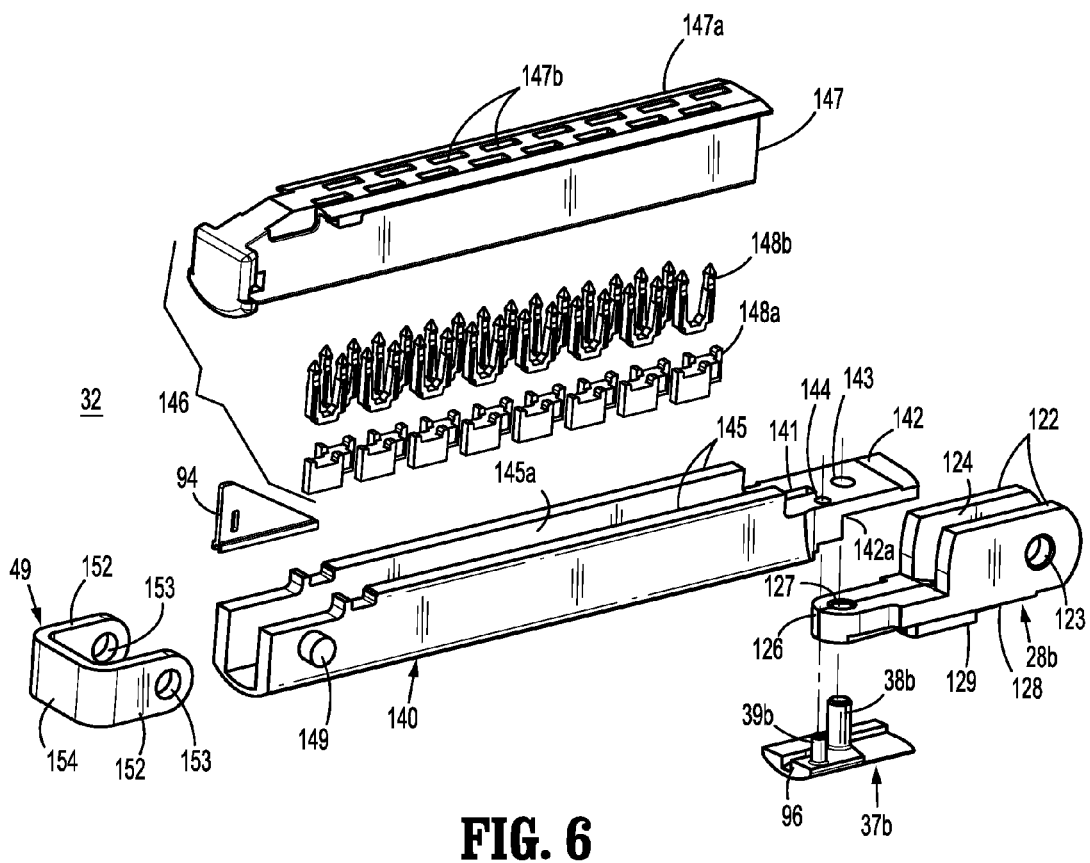
FIG. 6 is an exploded view, with parts separated, of the fastener jaw of FIG. 4.

With particular reference to FIG. 6, the lower cam member 28b includes sidewalls 122, a support arm 126, a camming surface 128, and a clamp stop 129. The sidewalls 122 each define a pivot hole 123 that is transverse to a longitudinal axis of the housing 20 (FIG. 1). The sidewalls 122 define a channel 124 therebetween. The support arm 126 extends distally from the sidewalls 122 and defines a rotation hole 127. The camming surface 128 and the clamp stop 129 are disposed on a lower surface of the sidewalls 122. The clamp stop 129 is positioned at a distal end of the camming surface 128 and extends below the camming surface 128. As shown the clamp stop 129 is positioned distal of the pivot hole 123; however, it is contemplated that the clamp stop 129 may be positioned proximal of the pivot hole 123.

Figure 3:
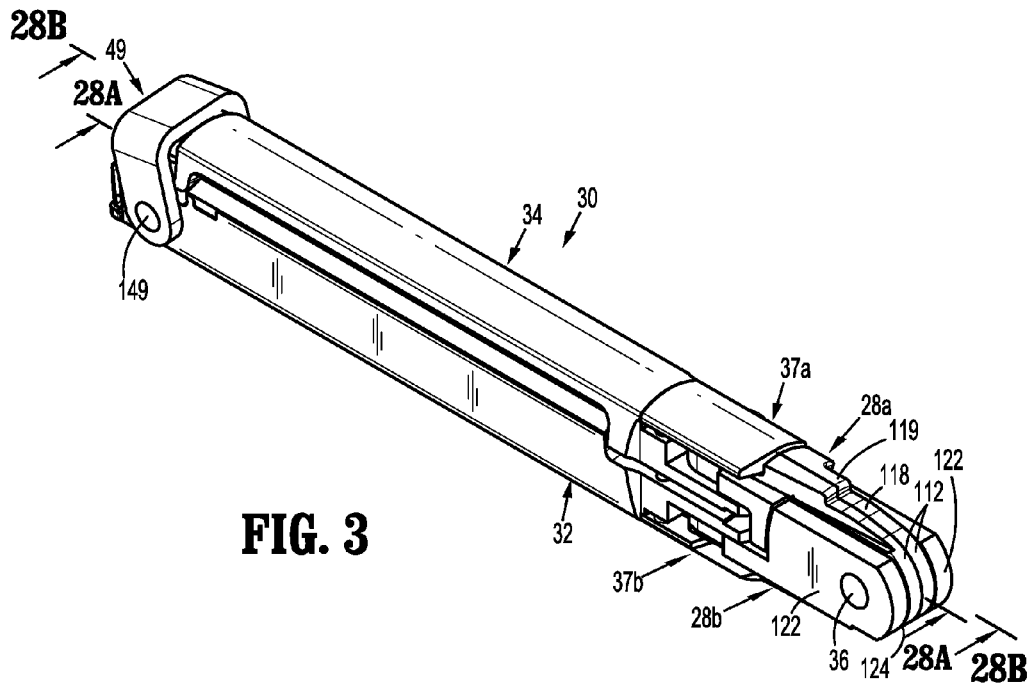
FIG. 3 is an enlarged view of the indicated area of detail of FIG. 2.
Figure 4:
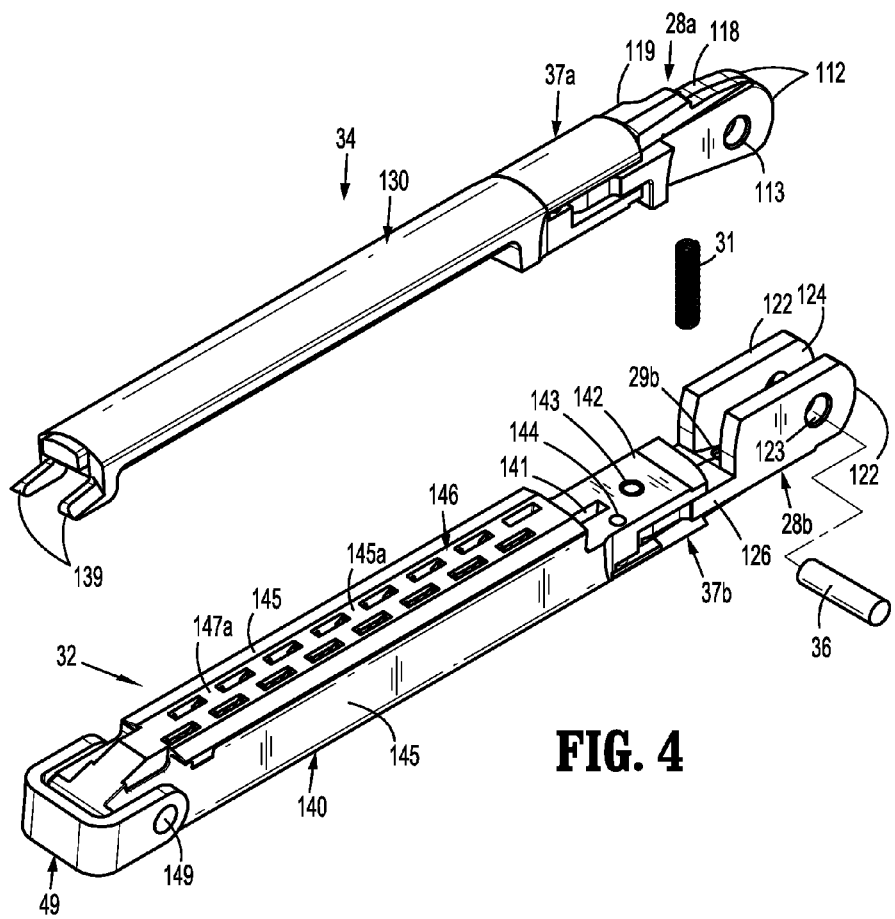
FIG. 4 is an exploded view, with parts separated, of the end effector of FIG. 3.

As shown in FIG. 3, the channel 124 of the lower cam member 28b receives the sidewalls 112 of the upper cam member 28a such that the pivot holes 113 of the upper cam member 28a are aligned with the pivot holes 123 of the lower cam member 28b. A pivot pin 36 (FIG. 4) is positioned within the pivot holes 113, 123 such that the cam members 28a, 28b are pivotal relative to one another about a pivot axis defined by the pivot pin 36.

With particular reference to FIG. 5, the retainer jaw 34 includes a body 130 that has a proximal tab 132, a central portion 135, and locking fingers 139. The proximal tab 132 defines a rotation opening 133 and an articulation opening 134. The rotation opening 133 is positioned within a recess 132a that is defined within the proximal tab 132. The rotation opening 133 and the articulation opening 134 each pass through an upper surface of the proximal tab 132 and may also pass through a lower surface of the proximal tab 132. The central portion 135 releasably receives a retainer cartridge 136 that includes a cartridge body 137 and retainers 138. The cartridge body 137 has a tissue contacting surface 137a that defines wells 137b that releasably receive retainers 138. The locking fingers 139 extend from a distal end of the central portion 135.

With particular reference to FIG. 6, the fastener jaw 32 includes a body 140 having a proximal tab 142, sidewalls 145, and protrusions 149. The proximal tab 142 defines a rotation opening 143 and an articulation opening 144. The rotation opening 143 and the articulation opening 144 each pass through a lower surface of the proximal tab 142 and may also pass through an upper surface of the proximal tab 142. The sidewalls 145 define a cartridge channel 145a that releasably receives a fastener cartridge 146 that includes a cartridge body 147. The cartridge body 147 has a tissue contacting surface 147a that defines openings 147b. The cartridge body 147 includes pushers 148a and fasteners 148b. A sled 94 is disposed within the cartridge channel 145a and is translatable through a sled channel 141 defined by the body 140 to eject the fasteners 148b from the fastener cartridge 146 as detailed below. The protrusions 149 are disposed on an outer surface of the sidewalls 145 adjacent a distal end of the body 140. The protrusions 149 rotatably support a locking member 49.

The locking member 49 includes legs 152 and a backspan 154 connecting the legs 152. Each of the legs 152 defines an opening 153 that is sized to receive and rotate about one of the protrusions 149. As detailed below, the locking member 49 is rotatable over the locking fingers 139 of the retainer jaw 34 to secure the fastener and retainer jaws 32, 34 in the closed configuration.

With continued reference to FIGS. 3-6, the upper coupling member 37a rotatably couples the retainer jaw 34 to the upper cam member 28a. The upper coupling member 37a includes a rotation post 38a and an articulation post 39a. The rotation post 38a of the upper coupling member 37a passes through the rotation hole 117 of the upper cam member 28a and is press-fit into the rotation opening 133 of the retainer jaw 34 to rotatably couple the retainer jaw 34 to the upper cam member 28a. The rotation post 38a of the upper coupling member 37a defines an articulation axis of the retainer jaw 34. When the articulation post 38a of the upper coupling member 37a is press-fit into the rotation opening 133 of the retainer jaw 34, the upper coupling member 37a is received in the recess 132a defined by the proximal tab 132 of the retainer jaw 34 such that an outer surface of the upper coupling member 37a is contiguous with an outer surface of the central portion 135 of the retainer jaw 34. Further, when the retainer jaw 34 is in a straight configuration, as detailed below, the outer surface of the upper coupling member 37a may be contiguous with the clamp stop 119 of the upper cam member 28a. The articulation post 39a of the upper coupling member 37a is disposed in the articulation opening 134 of the retainer jaw 34 to rotatably fix the upper coupling member 37a relative to the retainer jaw 34.

The lower coupling member 37b rotatably couples the fastener jaw 32 to the lower cam member 28b. The lower coupling member 37b includes a rotation post 38b and an articulation post 39b. The rotation post 38b of the lower coupling member 37b passes through the rotation hole 127 of the lower cam member 28b and is press-fit into the rotation opening 143 of the fastener jaw 32 to rotatably couple the fastener jaw 32 to the lower cam member 28b. The rotation post 38b of the lower coupling member 37b defines an articulation axis of the fastener jaw 32. When the articulation post 38b of the lower coupling member 37b is press-fit into the rotation opening 143 of the fastener jaw 32, the lower coupling member 37b is received in a recess 142a defined by the proximal tab 142 of the fastener jaw 32 such that an outer surface of the lower coupling member 37b is contiguous with an outer surface of the central portion 145 of the fastener jaw 32. Further, when the fastener jaw 32 is in a straight configuration, as detailed below, the outer surface of the lower coupling member 37b may be contiguous with the clamp stop 129 of the lower cam member 28b. The articulation post 39b of the lower coupling member 37b is disposed in the articulation opening 144 of the fastener jaw 32 to rotatably fix the lower coupling member 37b relative to the fastener jaw 32.

Referring briefly back to FIG. 2, the housing 20 includes an articulation mechanism 50, a clamping mechanism 60, and a firing mechanism 80 that manipulate the end effector 30 as detailed below. With additional reference to FIGS. 7-11, the articulation mechanism 50 includes an articulation shaft 52, an articulation pivot arm 56, and articulation rods 58. The articulation shaft 52 has a body 52a, a proximal flag 53 and a distal arm 54. The body 52a of the articulation shaft 52 is disposed parallel to a longitudinal axis of the housing 20 and is offset from the longitudinal axis of the housing 20. The distal arm 54 of the articulation shaft 52 is longitudinally offset from the body 52a of the articulation shaft 52 and is disposed along the longitudinal axis of the housing 20 and has a distal end 54a. The distal arm 54 of the articulation shaft is also vertically offset (e.g., below) the body 52a of the articulation shaft 52.

Figure 9:
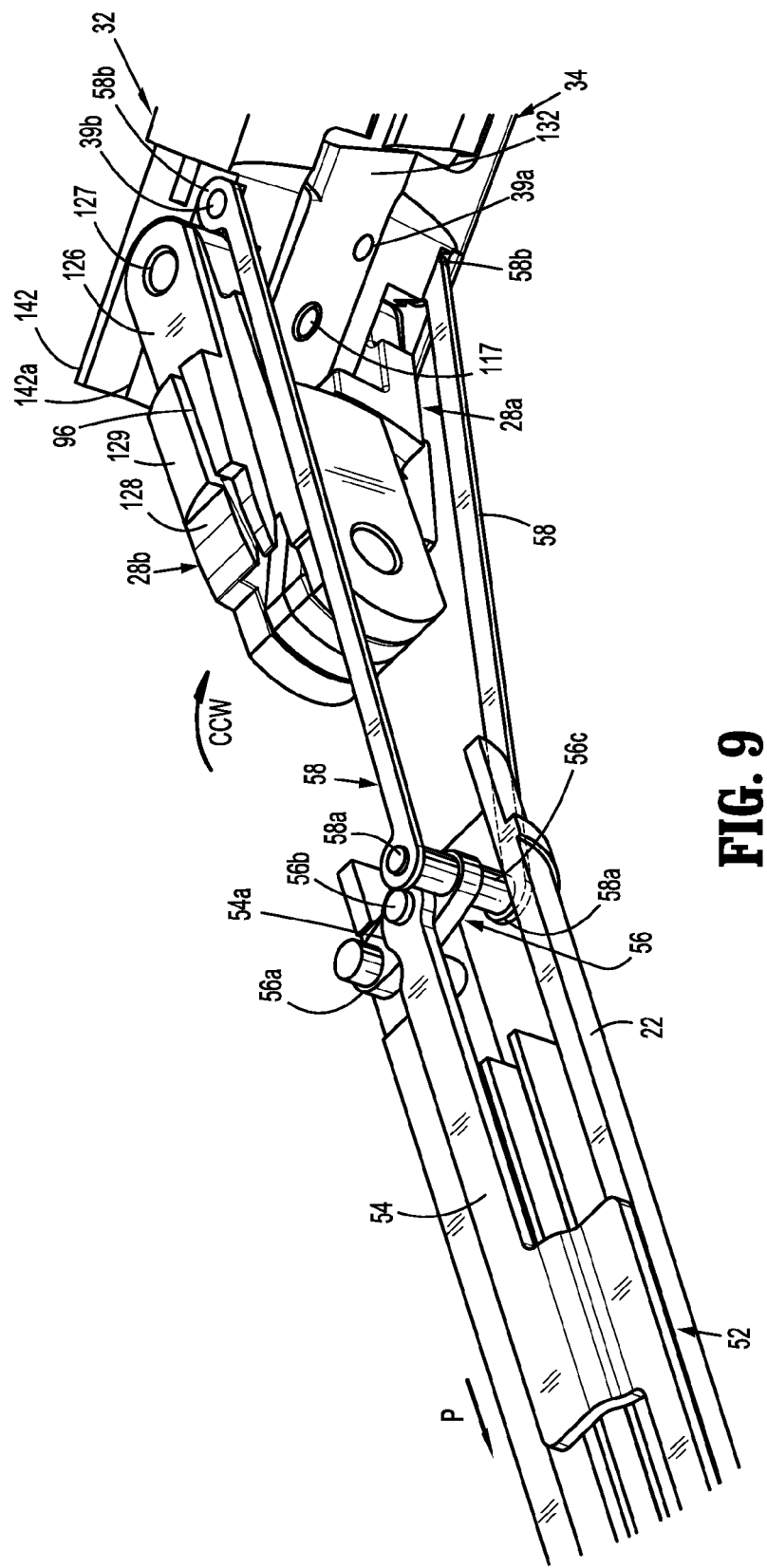
FIG. 9 in an enlarged view of the indicated area of detail of FIG. 7.

With particular reference to FIG. 9, the articulation pivot arm 56 includes a first pivot 56a, a second pivot 56b, and a third pivot 56c. The first pivot 56a is positioned on one end of the articulation pivot arm 56, the third pivot 56c is positioned on the other end of the articulation pivot arm 56, and the second pivot 56b is positioned between the first and third pivots 56a, 56c. The first pivot 56a of the articulation pivot arm 56 is rotatably supported by the upper housing portion 22 and may also be rotatably supported by the lower housing portion 21 (FIG. 2). The second pivot 56b is coupled to the distal end 54a of the distal arm 54 of the articulation shaft 52. The third pivot 56c is coupled to a proximal end 58a of each of the articulation rods 58. As shown, the proximal ends 58a of the articulation rods 58 are coupled to the upper and lower ends of the third pivot 56c; however, it is contemplated that the proximal ends 58a of the articulation rods 58 may be positioned anywhere along the third pivot 56c an equal distance in opposing directions from the pivot arm 56. The articulation rods 58 each include a distal end 58b that is coupled to a respective one of the articulation posts 39a, 39b of the upper and lower coupling members 37a, 37b.

Figure 10:
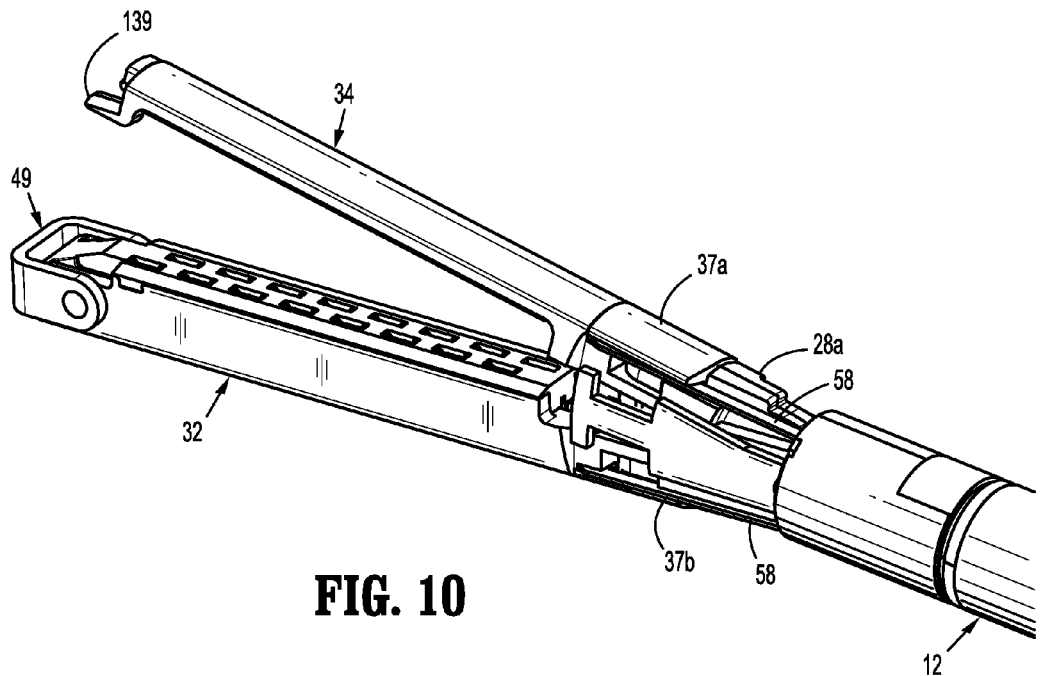
FIG. 10 is a perspective view of the end effector of FIG. 3 in a straight configuration.

With particular reference to FIG. 10, the end effector 30 is in a straight configuration such that the fastener and retainer jaws 32, 34 are substantially aligned with the elongated body 12 of the loading unit 10. In the straight configuration of the end effector 30, a longitudinal axis of the fastener and retainer jaws 32, 34 is substantially aligned with a longitudinal axis of the elongated body 12. In the straight configuration, an angle defined between the longitudinal axis of the end effector 30 and the longitudinal axis of the elongated body 12 is in a range of about 175° to about 185° (e.g., 180°). In other words, the longitudinal axis of the end effector 30 may be articulated in a range of about 5° to about −5° (e.g., 0°) from the longitudinal axis of the elongated body 12 in the straight configuration.

Figure 11:
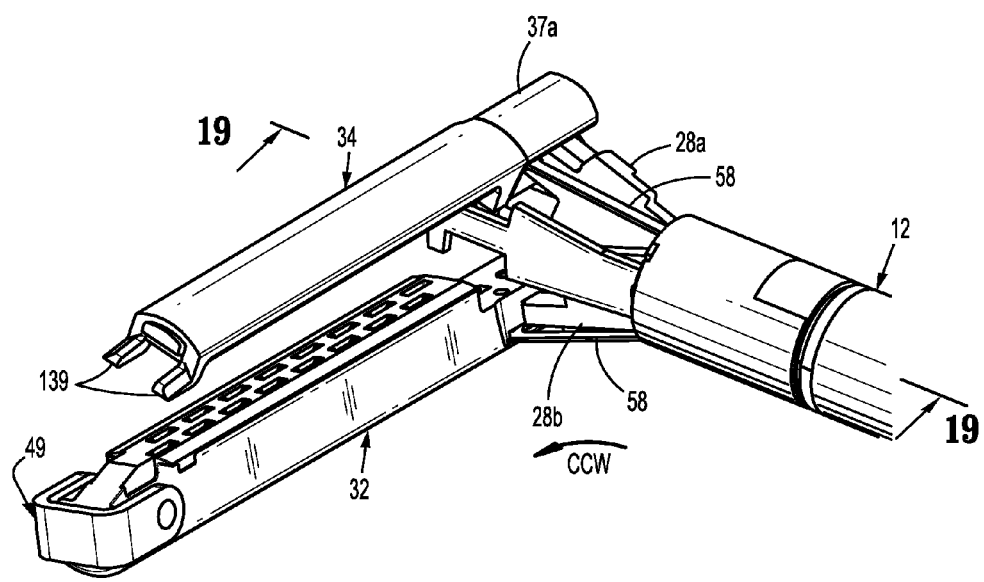
FIG. 11 is a perspective view of the end effector of FIG. 10 in a fully articulated configuration.
Figure 14:
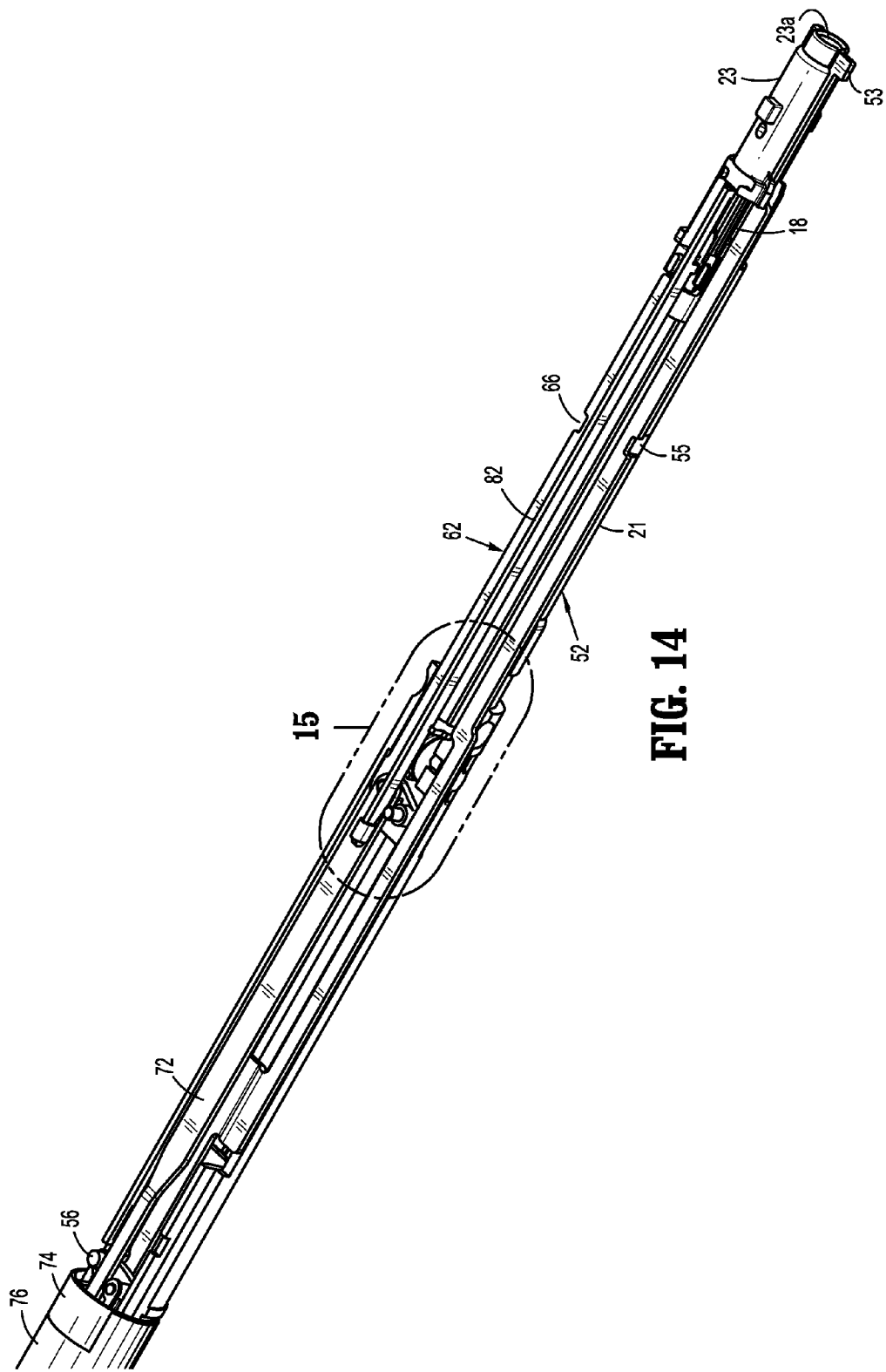
FIG. 14 is an upper perspective view of the loading unit of FIG. 1 with the upper housing portion removed.
Figure 15:
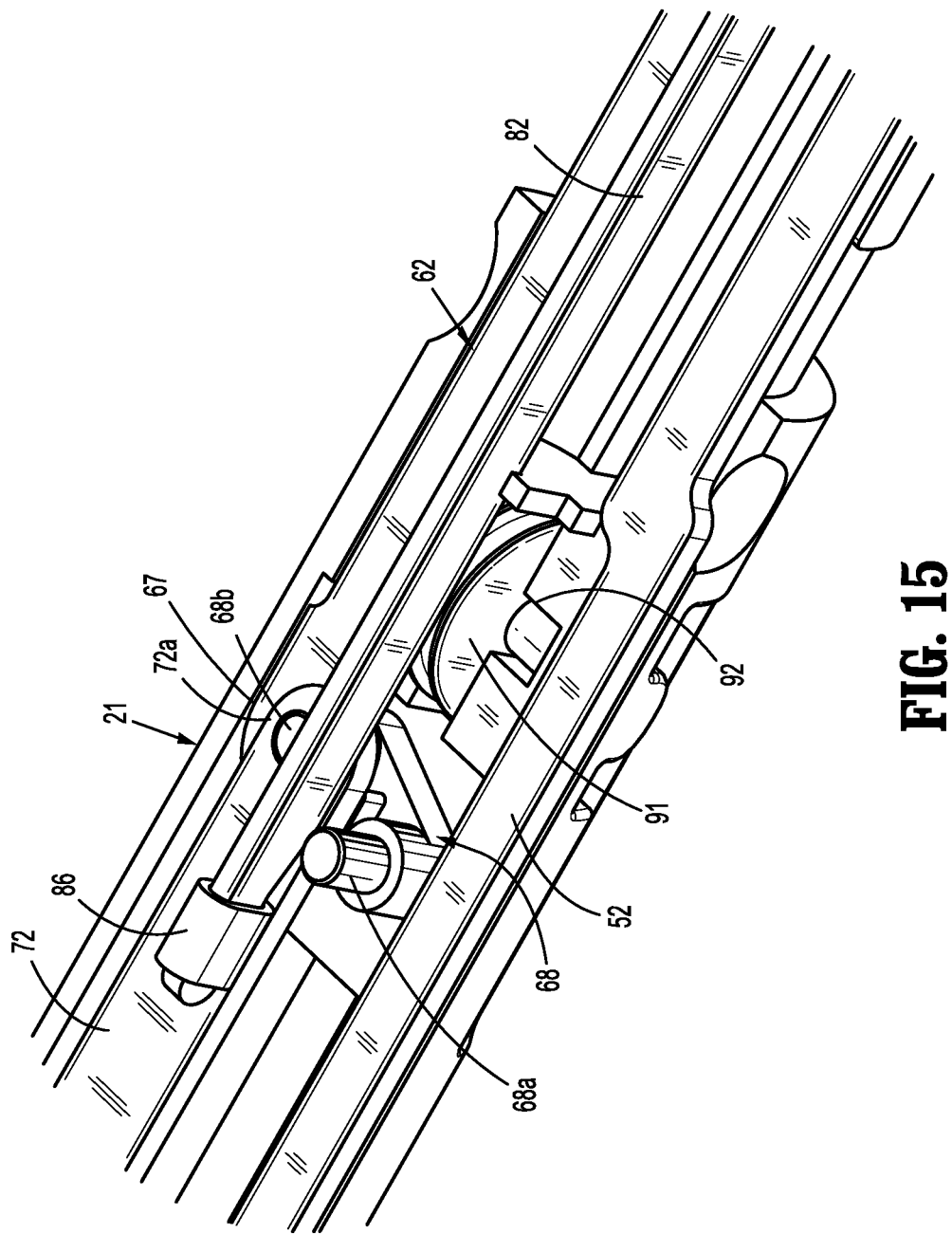
FIG. 15 is an enlarged view of the indicated area of detail of FIG. 14.

With particular reference to FIG. 11, the end effector 30 is in a fully articulated configuration such that the fastener and retainer jaws 32, 34 are articulated in relation to the upper and lower cam members 28a, 28b. As such, the fastener and retainer jaws 32, 34 are articulated relative to the pivot axis defined by the pivot pin 36. In the fully articulated configuration of the end effector 30, the fastener and retainer jaws 32, 34 are also articulated relative to elongated body 12 of the loading unit 10. Accordingly, the longitudinal axis of the fastener and retainer jaws 32, 34 defines an angle with the longitudinal axis of the elongated body 12 in the fully articulated configuration of the end effector 30. In the fully articulated configuration, the angle defined between the longitudinal axis of the fastener and retainer jaws 32, 34 and the longitudinal axis of the elongated body 12 is in a range of about 30° to about 105° (e.g., 90°). It will be appreciated that the end effector 30 may be articulated at any angle between the straight configuration and the fully articulated configuration. As detailed in greater detail below, the body 52a of the articulation shaft 52 defines an articulation locking notch 55 (FIG. 2) that is engaged by the shipping lock 40 (FIG. 1) to lock the loading unit 10 in a shipping configuration (FIG. 1) which is between the straight configuration and the fully articulated configuration of the end effector 30.

With continued reference to FIGS. 8-11, the proximal flag 53 of the actuation shaft 52 is longitudinally translatable in an articulation channel 57 (FIG. 2) defined in the connector 23 to articulate the fastener and retainer jaws 32, 34 of the end effector 30 between the straight configuration (FIG. 10) and the fully articulated configuration (FIG. 11). As the articulation flag 53 of the articulation shaft 52 is translated proximally, the articulation shaft 52 is translated proximally within the housing 20 as indicated by arrow P to rotate the pivot arm 56 in a counter-clockwise direction as indicated by arrow CCW (note that FIG. 9 is a bottom view of the end effector 30) to articulate the end effector 30 towards the fully articulated configuration. As the articulation shaft 52 is translated proximally, the fastener and retainer jaws 32, 34 are rotated about the rotation posts 38a, 38b (FIGS. 5 and 6) of the upper and lower coupling members 37a, 37b, respectively, to articulate the fastener and retainer jaws 32, 34 relative to the upper and lower cam members 28a, 28b. Specifically, as the articulation shaft 52 is translated proximally, the distal end 54a of the distal arm 54 moves the second pivot 56b of the pivot arm 56 to rotate the pivot arm 56 about the first pivot 56a in the counter-clockwise direction. As the pivot arm 56 is rotated in the counter-clockwise direction, the third pivot 56c moves the proximal ends 58a of the articulation rods 58 to translate the articulation rods 58 proximally. As the articulation rods 58 are translated proximally, the distal end 58b of each articulation rod 58 moves a respective one the articulation posts 39a, 39b of the upper and lower coupling members 37a, 37b to articulate the fastener and retainer jaws 32, 34 of the end effector 30 towards the fully articulated configuration in the counter-clockwise direction. It will be appreciated that the pivot arm 56 acts as a lever to multiply the translation of the articulation rods 58 with respect to the translation of the articulation shaft 52.

As the articulation flag 53 of the articulation shaft 52 is translated distally, the articulation shaft 52 is translated distally within the housing 20 in a direction opposite arrow P to rotate the pivot arm 56 in a clockwise direction opposite arrow CCW to articulate the fastener and retainer jaws 32, 34 towards the straight configuration. As the articulation shaft 52 is translated distally, the fastener and retainer jaws 32, 34 are rotated about the rotation posts 38a, 38b of the upper and lower coupling members 37a, 37b, respectively. Specifically, as the articulation shaft 52 is translated distally, the distal end 54a of the distal arm 54 moves the second pivot 56b of the pivot arm 56 to rotate the pivot arm 56 about the first pivot 56a in the clockwise direction. As the pivot arm 56 is rotated in the clockwise direction, the third pivot 56c moves the proximal ends 58a of the articulation rods 58 to distally translate the articulation rods 58. As the articulation rods 58 are translated distally, the distal end 58b of each articulation rod 58 moves a respective one the articulation posts 39a, 39b of the upper and lower coupling members 37a, 37b to articulate the fastener and retainer jaws 32, 34 of the end effector 30 towards the straight configuration in the clockwise direction.

Referring to FIGS. 11-22, the clamping mechanism 60 (FIG. 2) moves the fastener and retainer jaws 32, 34 of the end effector 30 between an open configuration (FIG. 11) and a clamped configuration (FIG. 21) in a substantially parallel manner when the fastener and retainer jaws 32, 34 are in the fully articulated configuration. In the open configuration of the end effector 30, the fastener and retainer jaws 32, 34 are spaced-apart relative to one another. As detailed below, the end effector 30 may be secured in a shipping configuration (FIG. 1) by the shipping lock 40 (FIG. 1) such that the fastener cartridge 146 and the retainer cartridge 136 may be coupled to or decoupled from the fastener and retainer jaws 32, 34, respectively.

In the clamped configuration of the end effector 30, the tissue contacting surfaces 147a, 137a of the fastener and retainer cartridges 146, 136, respectively, oppose one another and each fastener 148b of the fastener cartridge 146 is aligned with a respective retainer 138 of the retainer cartridge 136. As detailed below, when the fasteners 148b are ejected from the fastener cartridge 146, the fasteners 148b form two-part fasteners with the retainers 138 through tissue between the tissue contacting surfaces 147a, 137a of the fastener and retainer jaws 146, 136, respectively.

With particular reference to FIGS. 2 and 12-14, the clamping mechanism 60 includes a clamping shaft 62, a clamping pivot arm 68, a clamping rod 72, a clamping actuator 74, a clamping sleeve 76, and a jaw support 78. The clamping shaft 62 includes a proximal portion 64 that defines a carriage notch 65 that receives a carriage 18 which is disposed within a carriage channel 23a defined in the connector 23. The carriage 18 is configured to translate in response to a drive rod (not shown) of a surgical instrument coupled to the connector 23.

Figure 16:
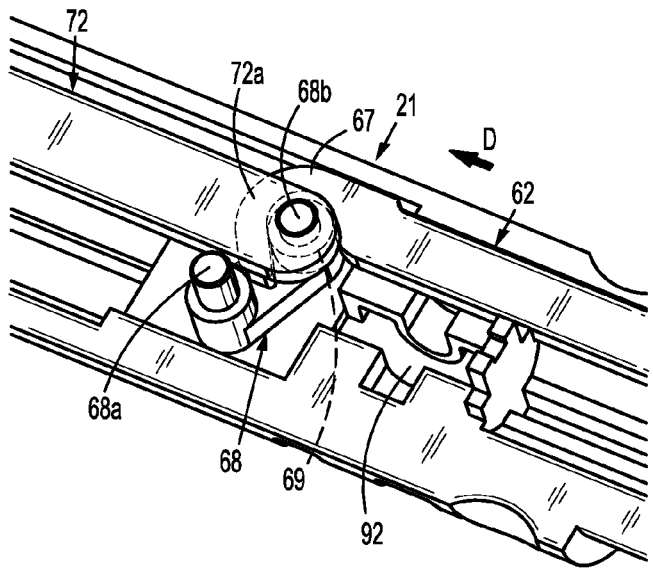
FIG. 16 is a perspective view of the clamping mechanism of FIG. 15 in an open configuration.
Figure 17:
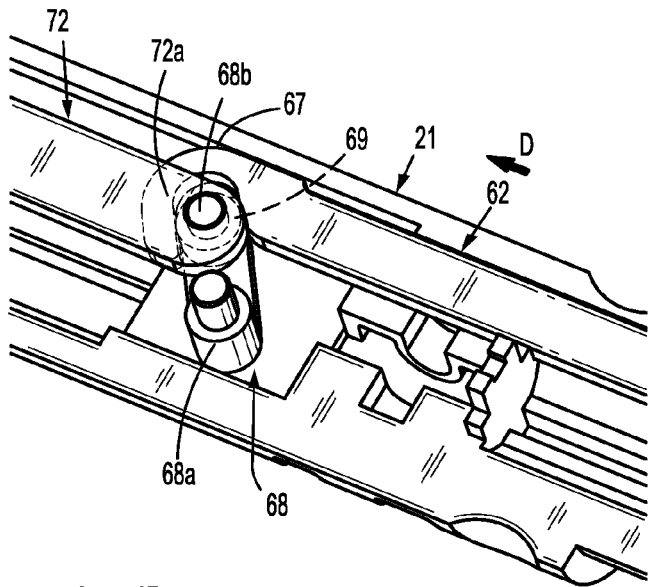
FIG. 17 is a perspective view of the clamping mechanism of FIG. 15 in a shipping configuration between the open configuration and a clamped configuration.
Figure 18:
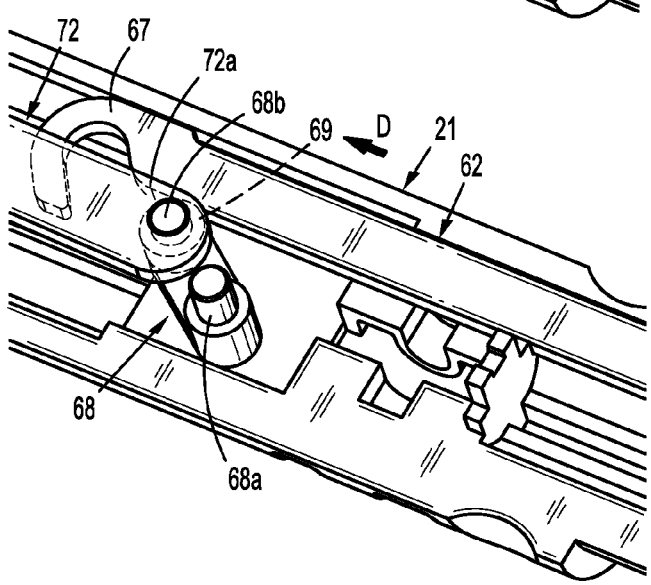
FIG. 18 is a perspective view of the clamping mechanism of FIG. 15 in the clamped configuration.

Now with reference to FIGS. 16-18, the clamping shaft 62 includes a distal portion which defines a cam or clamping hook 67. The clamping hook 67 slidingly engages the clamping pivot arm 68 to pivot the clamping pivot arm 68 between an open position (FIG. 16) corresponding to the open configuration of the fastener and retainer jaws 32, 34 of the end effector 30 (FIG. 19) and a clamped position (FIG. 18) corresponding to the clamped configuration of the fastener and retainer jaws 32, 34 of the end effector 30 (FIG. 20). The clamping pivot arm 68 includes a first end 68a, a second end 68b, and a cam follower or engagement portion 69 positioned between the first end 68a and the second end 68b. The clamping pivot arm 68 is rotatable about the first end 68a which is rotatably secured by the lower housing portion 21 of the inner housing 20 (FIG. 1). The first end 68a of the clamping pivot arm 68 may also be rotatably secured by the upper housing portion 22 (FIG. 2) of the inner housing 20. The second end 68b is rotatably coupled to a proximal end 72a of the clamping rod 72. The engagement portion 69 is engaged by the clamping hook 67 of the clamping shaft 62 to rotate the clamping pivot arm 68 about its first end 68a. As the clamping pivot arm 68 pivots about its first end 68a, the clamping pivot arm 68 translates the clamping rod 72. As the clamping shaft 62 is advanced in the direction indicated by arrow D, the clamping hook 67 cams the engagement portion 69 of the clamping pivot arm 68 to rotate the clamping pivot arm 68 towards the clamped position (FIG. 18). As the clamping shaft 62 is retracted in a direction opposite arrow D, the clamping hook 67 cams the engagement portion 69 of the clamping pivot arm 68 to rotate the clamping pivot arm 68 towards the open position (FIG. 16). The clamping hook 67 of the clamping shaft 62 may be advanced past the clamping pivot arm 68 such that the clamping pivot arm 68 remains in the clamped position (FIG. 18) until the clamping shaft 62 is retracted such that the clamping hook 67 reengages the engagement portion 69 of the clamping pivot arm 68. The clamping shaft 62 defines a clamping lock notch 66 (FIG. 13) that is engagable by the shipping lock 40 (FIG. 1) to secure the clamping mechanism 60 in a shipping position, which is between the open and closed positions corresponding to the shipping configuration of the loading unit 10.

Figure 19:
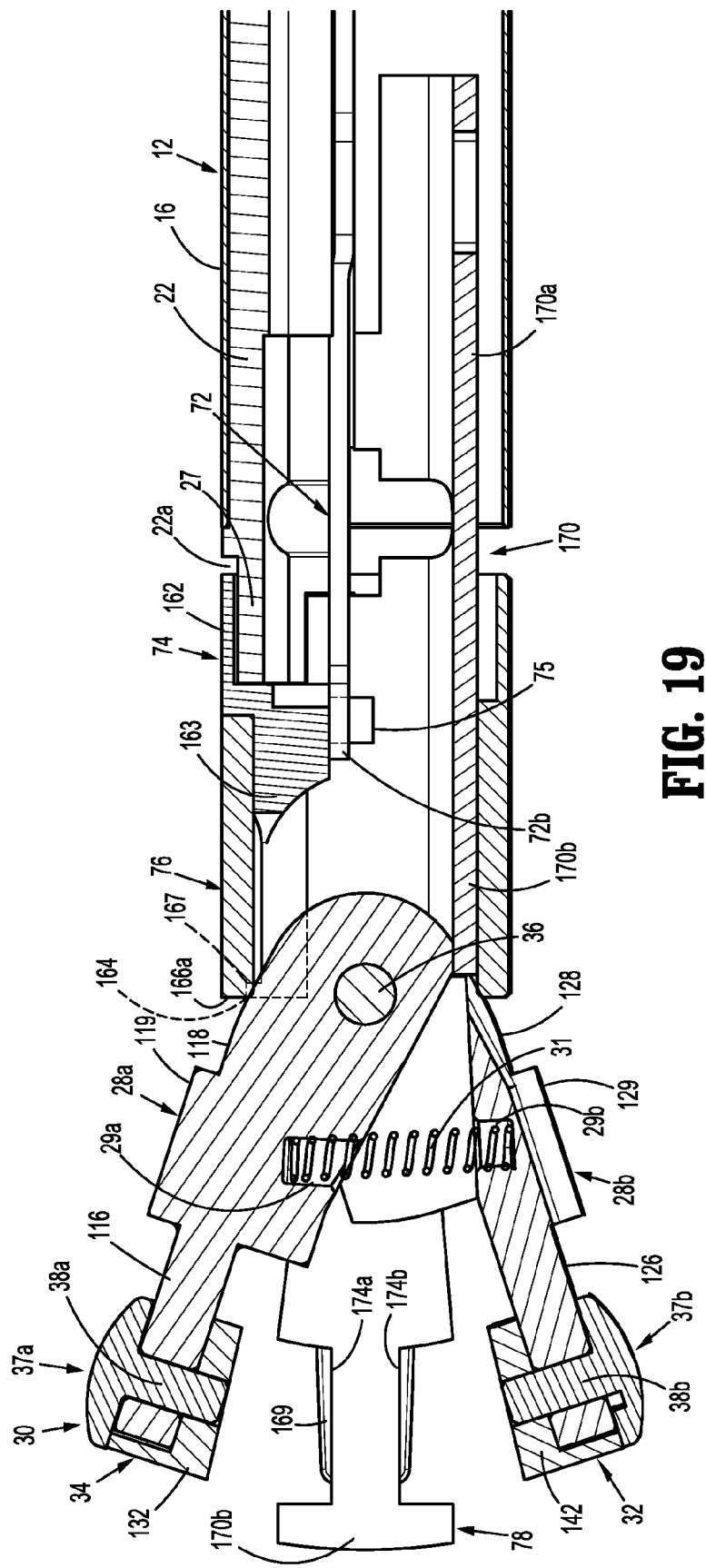
FIG. 19 is a cross-sectional view taken along section line 19-19 of FIG. 11.
Figure 20:
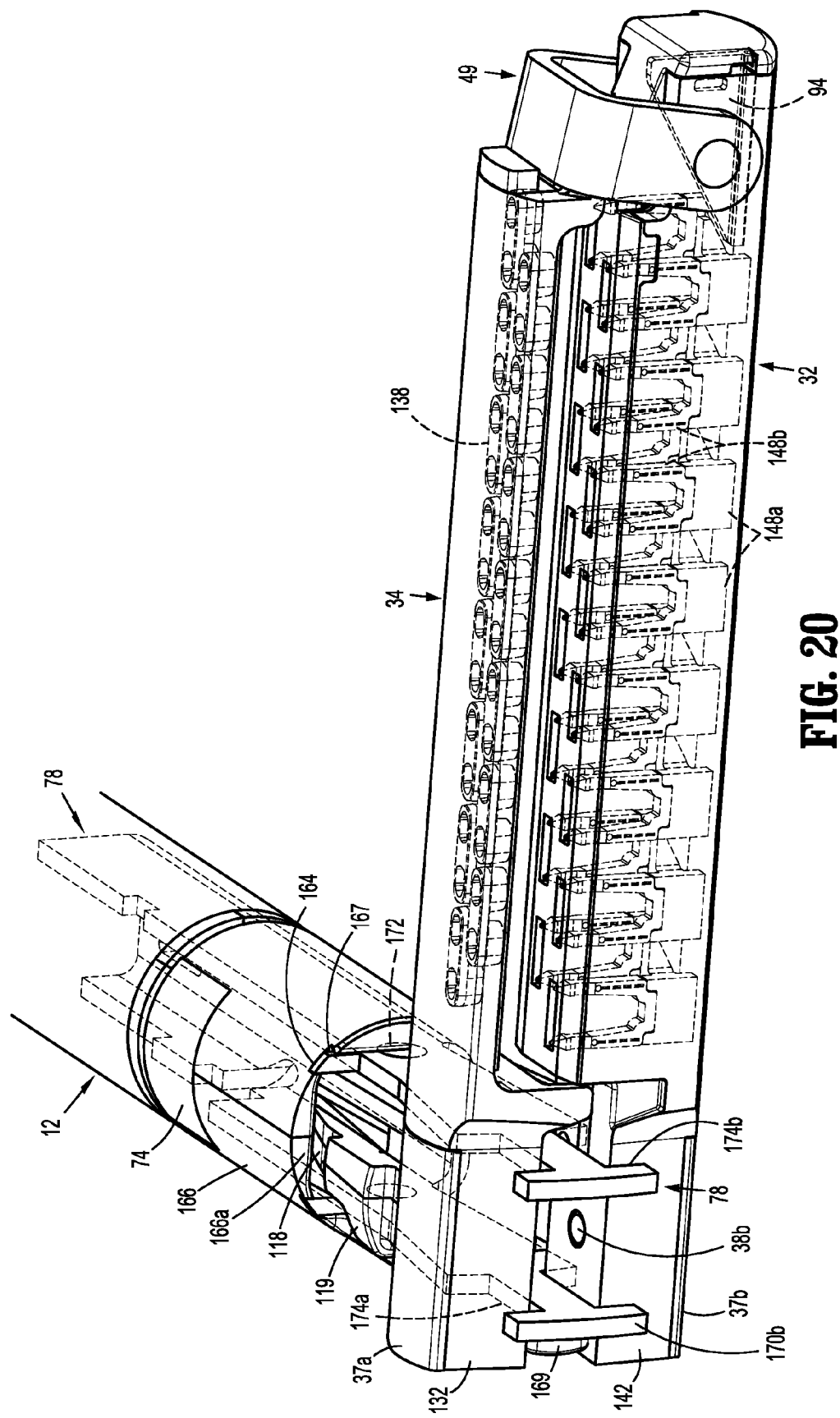
FIG. 20 is a front perspective view of a distal portion of the loading unit and end effector of FIG. 1 in the fully articulated and clamped configuration.
Figure 21:
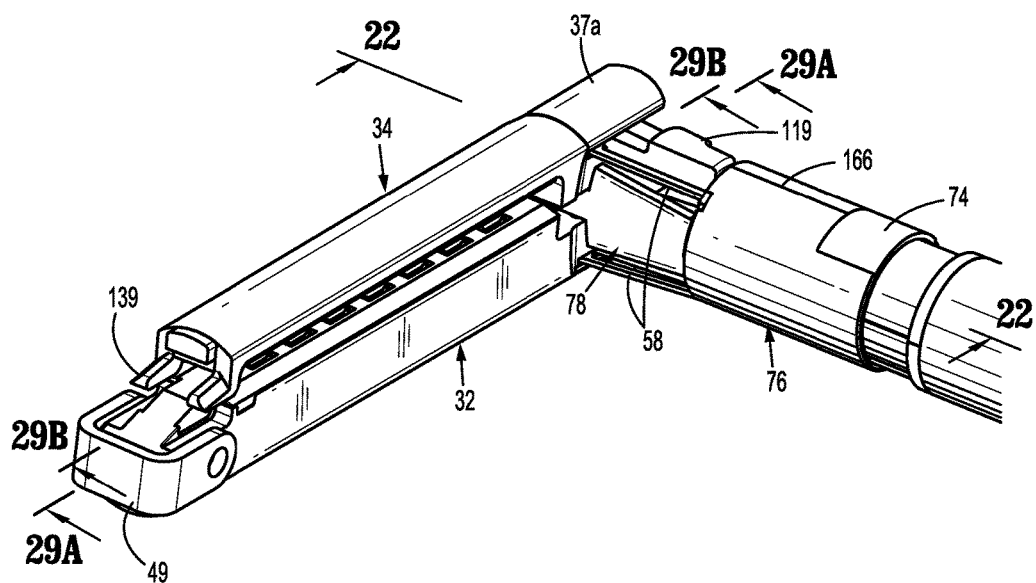
FIG. 21 is a rear perspective view of a distal portion of the loading unit and end effector of FIG. 1 in the fully articulated and clamped configuration.
Figure 22:
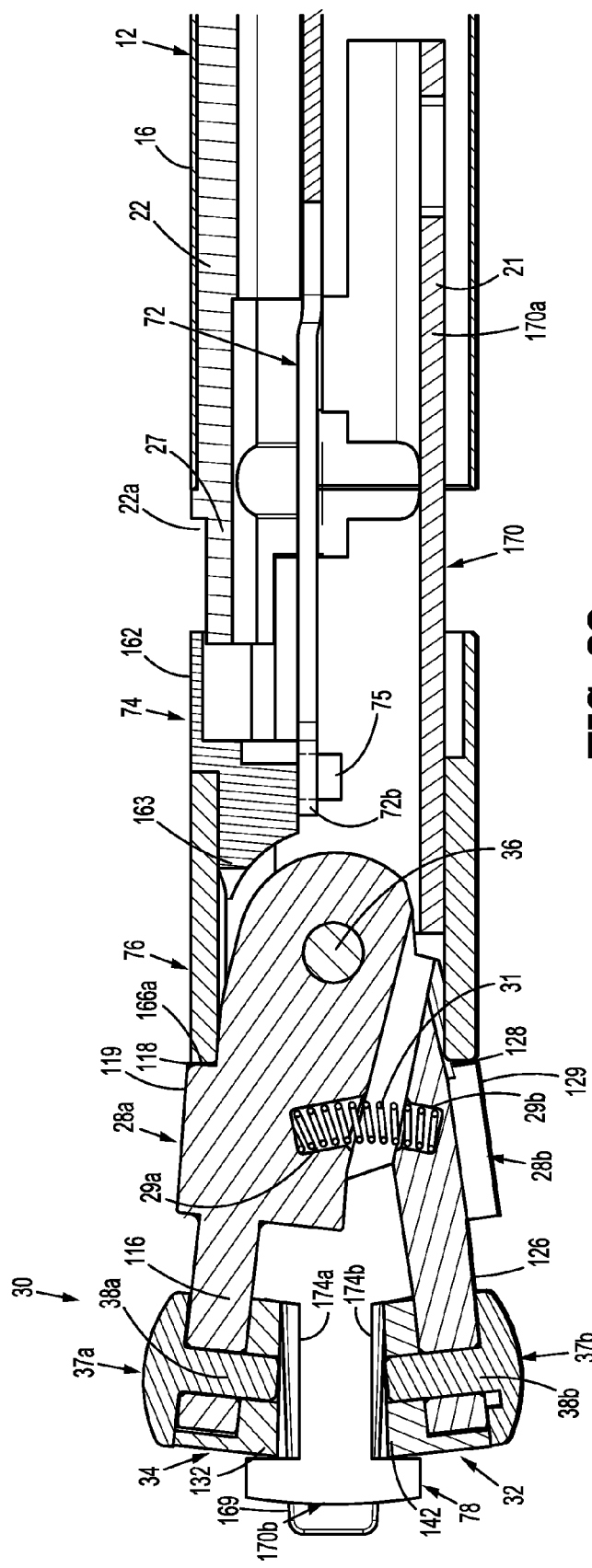
FIG. 22 is a cross-sectional view taken along the section line 22-22 of FIG. 21.
Figure 23:
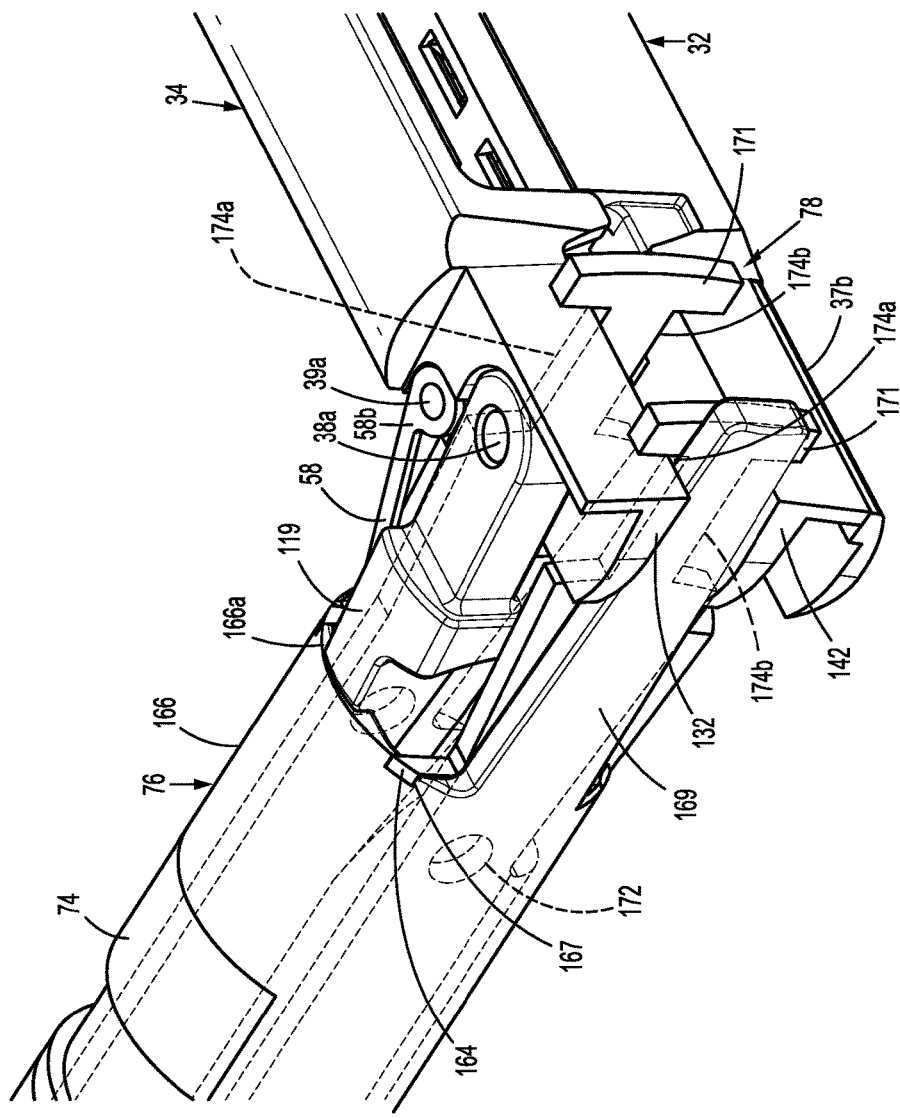
FIG. 23 is a perspective view of the end effector of FIG. 21 with the upper coupling member removed.

With particular reference to FIGS. 13 and 19, the distal end 72b of the clamping rod 72 is coupled to a clamping post 75 of the clamping actuator 74. The distal end 72b of the clamping rod 72 may define an opening that receives the clamping post 75. As the clamping pivot arm 68 is pivoted between its open and clamped positions, the clamping rod 72 moves the clamping actuator 74 between a proximal position (FIG. 19) and a distal position (FIG. 22). The clamping actuator 74 includes a proximal body 162 and retraction arms 163. In its proximal position, the proximal body 162 is positioned over the distal extension 27 of the upper housing portion 22. The upper housing portion 22 may define a recess 22a that is sized to receive the proximal body 162 of the clamping actuator 74. An outer surface of the proximal body 162 is aligned with an outer surface of the distal tube 16 and is coincident with an outer surface of the clamping sleeve 76. The retraction arms 163 extend distally from the proximal body 162 and include an engagement finger 164 at a distal end of each retraction arm 163. The retraction arms 163 extend within the clamping sleeve 76 such that the engagement fingers 164 engage retraction recesses 167 defined in a distal end 166a of the clamping sleeve 76.

The clamping sleeve 76 includes a tubular body 166 and a clamp stop arm 169. The tubular body 166 defines a proximal cavity 168 that receives the clamping actuator 74 such that the clamping actuator 74 forms a contiguous outer surface with the tubular body 166. The proximal cavity 168 is defined in an upper surface of the tubular body 166. The clamp stop arm 169 extends distally from the distal end 166a of the tubular body 166 and is positioned to extend between the proximal tabs 142, 132 (FIG. 22) of the fastener and retainer jaws 32, 34, respectively, when the fastener and retainer jaws 32, 34 are in the fully articulated configuration and the clamping sleeve 76 is in a distal position.

With particular reference to FIGS. 19 and 22, the clamping sleeve 76 is translatable between a proximal position (FIG. 19) and a distal position (FIG. 22) to move the end effector 30 between the open and clamped configurations. As detailed below, the tubular body 166 of the clamping sleeve 76 engages camming surfaces 118, 128 of the upper and lower cam members 28a, 28b, respectively, to move the fastener and retainer jaws 32, 34 towards the clamped configuration as the clamping sleeve 76 is translated towards its distal position.

In the proximal position of the clamping sleeve 76, the distal end 166a of the tubular body 166 is at or is proximal to the pivot pin 36. The upper and lower cam members 28a, 28b each define a portion of a biasing channel 29a, 29b that receives an end effector biasing member 31. The end effector biasing member 31 urges the support arms 116, 126 of the upper and lower cam members 28a, 28b, respectively, away from one another such that the fastener and retainer jaws 32, 34 are urged towards the open configuration.

As the clamping actuator 74 is moved towards its distal position by the clamping rod 72, the clamping actuator 74 translates the clamping sleeve 76 distally. As the clamping sleeve 76 is translated distally, the distal end 166a of the tubular body 166 engages the camming surfaces 118, 128 of the upper and lower cam members 28a, 28b to urge the support arms 116, 126 of the upper and lower cam members 28a, 28b, respectively, against the end effector biasing member 31 and towards one another to move the fastener and retainer jaws 32, 34 towards the clamped configuration. When the clamping sleeve 76 reaches its distal position, the distal end 166a of the tubular body 166 abuts the clamp stops 119, 129 of the upper and lower cam members 28a, 28b, respectively, such that the clamp stops 119, 129 act as a limit stop for the clamping sleeve 76 and defining a maximum travel distance for the clamping sleeve 76. In the distal position of the clamping sleeve 76, the proximal tabs 142, 132 of the fastener and retainer jaws 32, 34, respectively, engage the clamp stop arm 169.

As shown, as the fastener and retainer jaws 32, 34 move between the open and clamped configurations, the tissue contacting surfaces 137a, 147a maintain a substantially parallel relationship to one another. Specifically, the tissue contacting surfaces 137a, 147a close along an arc having a center defined on a pivot axis defined by the pivot pin 36. The support arms 116, 126 of the upper and lower cam members 28a, 28b extend from the pivot pin 36 to increase the radius of the arc such that the change in angle between the tissue contacting surface 137a of the retainer jaw 32 and the tissue contacting surface 147a of the fastener jaw is minimized as the fastener and retainer jaws 32, 34 move between the open and closed configurations such that the tissue contacting surfaces 137a, 147a maintain a substantially parallel relationship with one another.

With particular reference to FIGS. 13 and 22, the jaw support 78 is disposed within the housing 20 to support the end effector 30. The jaw support 78 includes a body 170 having sidewalls 171 that defines an end effector channel 172 therebetween. The body 170 has a proximal portion 170a that is supported with the housing 20 and a distal portion 170b that extends from the housing 20. Each sidewall 171 of the jaw support 78 defines a pivot support 172 (FIG. 20) that supports the pivot pin 36 (FIG. 3) which defines the pivot axis of the upper and lower cam members 28a, 28b between the proximal and distal portions 170a, 170b. The sidewalls 171 are disposed within the clamping sleeve 76 and are dimensioned such that the clamping sleeve 76 may translate between its proximal and distal positions without engaging the sidewalls 171. Each sidewall 171 defines upper and lower clamping pockets 174a, 174b in the distal portion 170b. the upper and lower clamping pockets 174a, 174b are dimensioned such that when the fastener and retainer jaws 32, 34 are in the clamped configuration, the proximal tabs 142, 132 of the fastener and retainer jaws 32, 34, respectively, engage a portion the clamp stop arm 169 positioned adjacent the upper and lower clamping pockets 174a, 174b of one of the sidewalls 171.

When the fastener and retainer jaws 32, 34 of the end effector 30 are in both the straight and fully articulated configurations, the sidewalls 171 allow the end effector 30 to pivot between the open and clamped configurations. In contrast, when the end effector 30 is in any configuration between the straight and fully articulated configurations, the proximal tabs 142, 132 of the fastener and retainer jaws 32, 34, respectively, engage the sidewalls 171 to prevent the end effector 30 from pivoting towards the clamped configuration. When the end effector 30 is in the straight configuration, the proximal tabs 142, 132 of the fastener and retainer jaws 32, 34, respectively, are positioned within the end effector channel 172 between the sidewalls 171 to allow the fastener and retainer jaws 32, 34 to pivot towards the clamped configuration. Additionally, if the fastener and retainer jaws 32, 34 of the end effector 30 are in both the clamped and straight configurations, the sidewalls 171 engage the proximal tabs 132, 142 of the fastener and retainer jaws 32, 34, respectively, to prevent articulation of the end effector 30. When the end effector 30 is in the fully articulated configuration, the proximal tabs 142, 132 of the fastener and retainer jaws 32, 34, respectively, are received within the upper and lower clamping pockets 174a, 174b of the sidewalls 171 to allow the fastener and retainer jaws 32, 34 to pivot towards the clamped configuration.

In any of the embodiments disclosed herein, an end effector includes a first jaw member, a second jaw member, and a pivot pin. The first jaw member includes a first camming member, and the second jaw member includes a second camming member. The pivot pin is positioned in first and second pivot holes such that the first and second jaw members are pivotable relative to one another in a substantially parallel manner between open and clamped configurations about the pivot pin. The first and second bodies are also articulatable relative to the first and second camming members about first and second articulation posts of each jaw member. In any of the embodiments disclosed herein, the first and second jaw members have camming surfaces on the first and second camming members (respectively), the camming surfaces are disposed proximal to the pivot pin when the jaw members are in the un-articulated position, and the camming surfaces are engaged by a clamping member (such as a clamping sleeve) to move the jaws to the clamped position.

Referring now to FIGS. 24-27, the firing mechanism 80 includes a firing rod 82 and a firing pulley 91 rotatably supported in the lower housing portion 21 (FIG. 15), a sled 94 slidingly disposed within the end effector 30, and a firing cable 81 extending from the firing rod 82 to the sled 94. The firing rod 82 includes a proximal firing flag 83a and a distal firing flag 83b positioned in a proximal portion of the firing rod 82. The proximal and distal firing flags 83a, 83b define a firing gap 84 between the proximal and distal firing flags 83a, 83b. The carriage 18 is received within the firing gap 84 between the proximal and distal firing flags 83, 83b. The firing rod 82 includes a distal portion 85 that has a distal finger 87. The firing cable 81 passes around the distal finger 87 and is secured to the distal finger 87 by a cable retainer 86 secured or crimped over the distal finger 87 and the firing cable 81.

Figure 24:
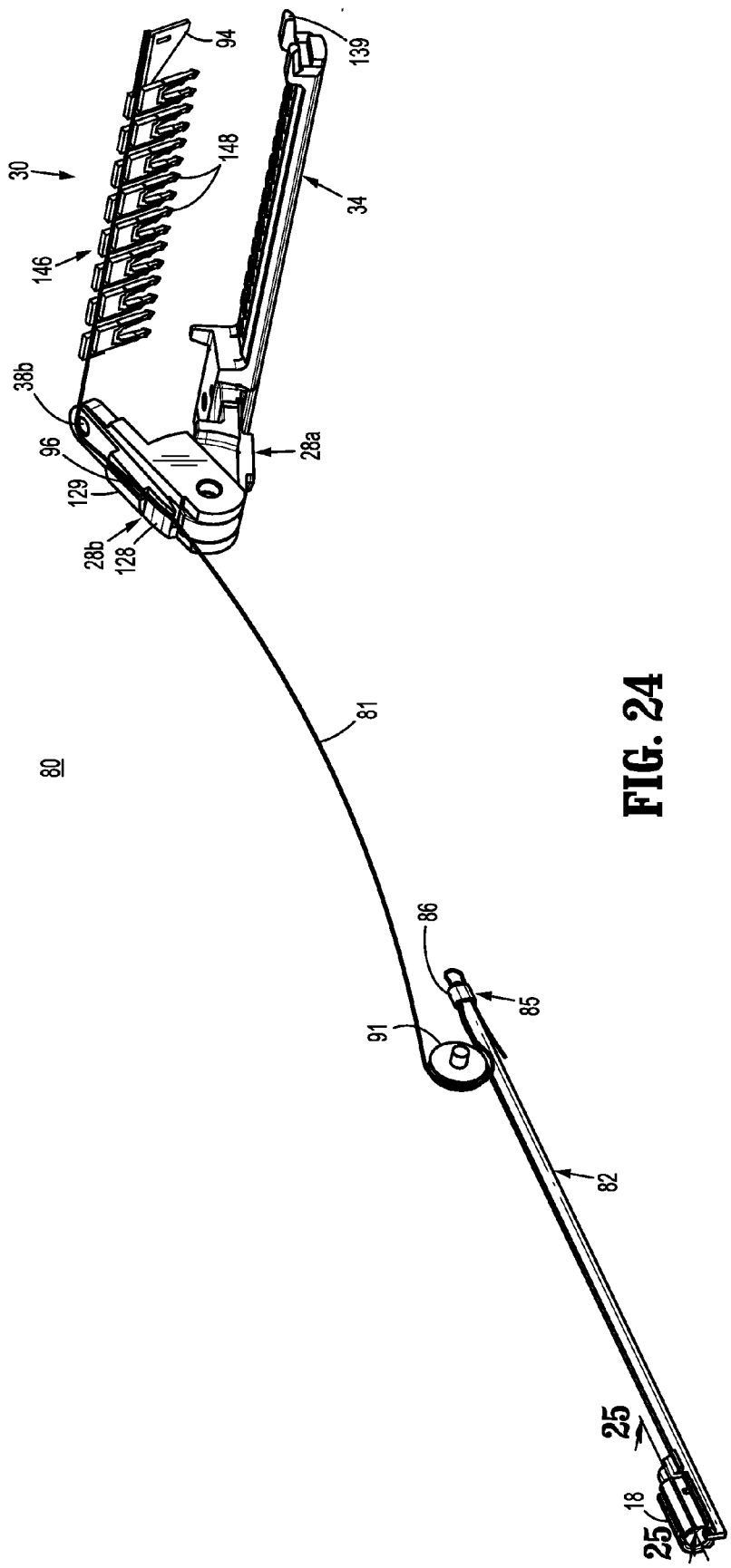
FIG. 24 is a perspective view of the firing assembly of the loading unit of FIG. 1.
Figure 27:
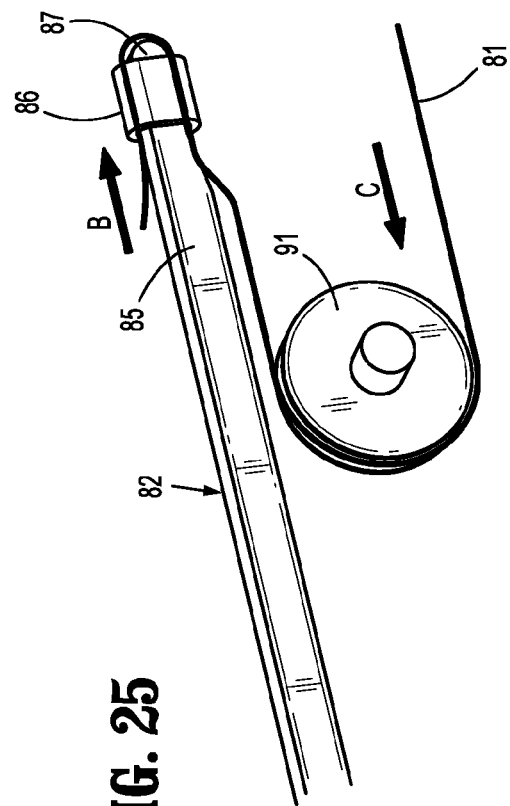
FIG. 27 is an enlarged view of a distal end the firing rod of the firing mechanism of FIG. 24.
Figure 25:
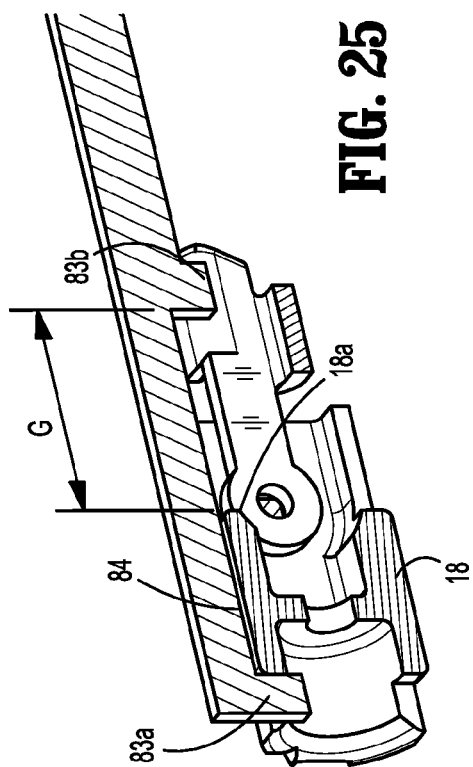
FIG. 25 is a cross-sectional view taken along the section line 25-25 of FIG. 24.
Figure 26:
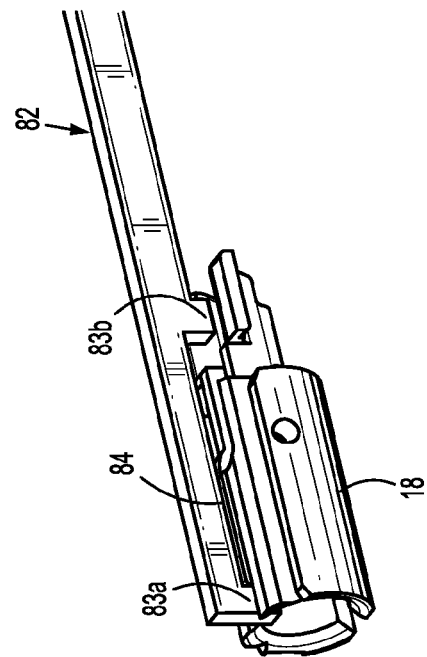
FIG. 26 is an enlarged view of a proximal end of a firing rod of the firing mechanism of FIG. 24.
Figure 29A:
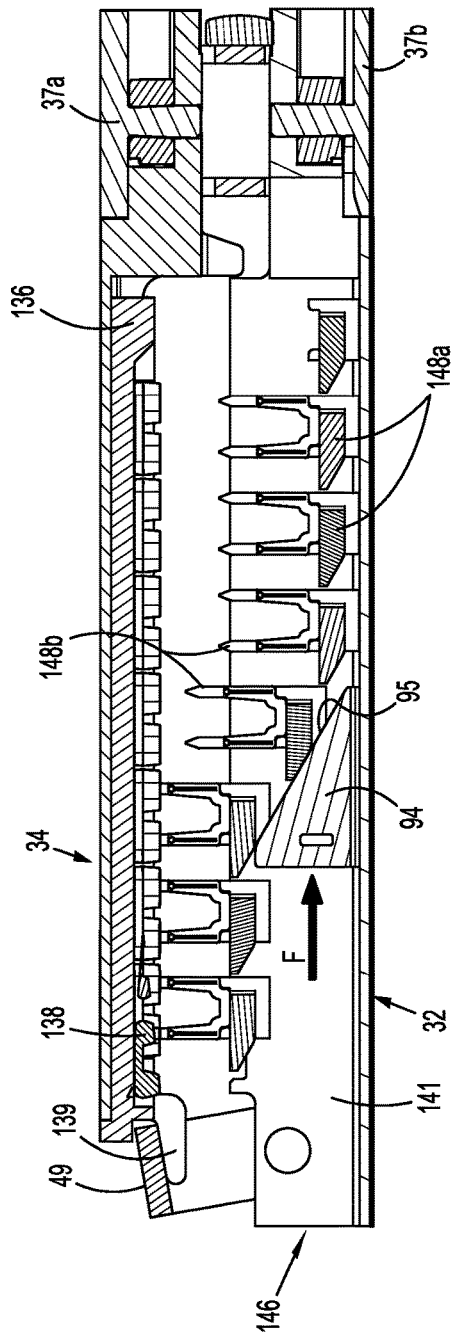
FIG. 29A is a cross-sectional view of the end effector of FIG. 28A with the sled partially pulled through the fastener cartridge.
Figure 29B:
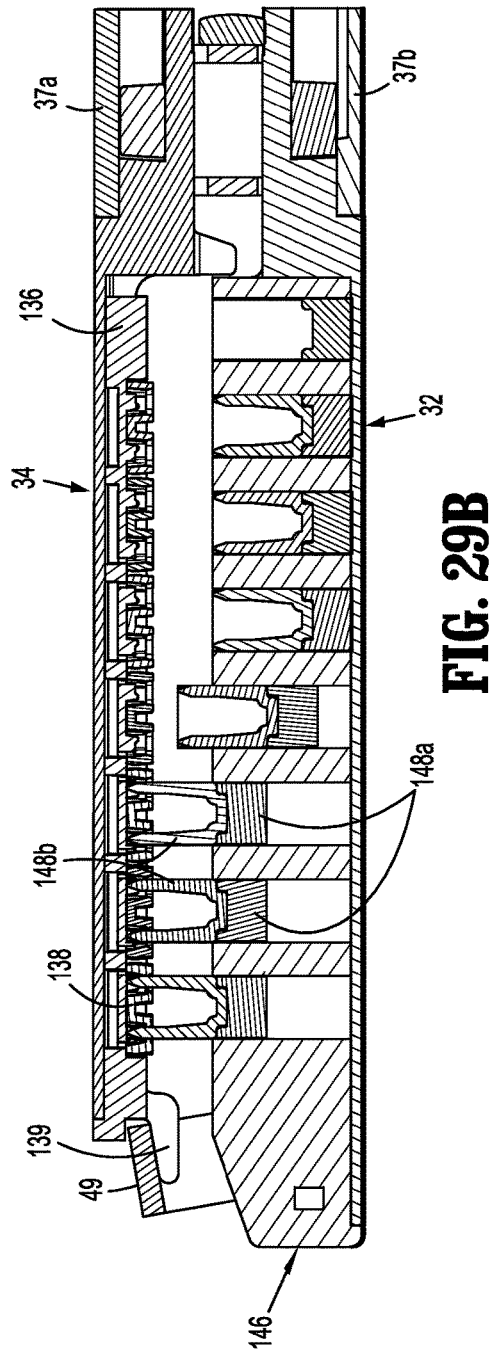
FIG. 29B is a cross-sectional view of the end effector of FIG. 28B with the sled partially pulled through the fastener cartridge to eject fasteners from the fastener cartridge and including the retainer jaw in the clamped position.

With particular reference to FIGS. 24 and 27, the firing cable 81 extends proximally from the distal finger 87 of the firing rod 82 and over the firing pulley 91 that is rotatably supported within a firing pulley opening 92 (FIG. 15) defined in the lower housing portion 21. The firing cable 81 extends distally from the firing pulley 91 and through a firing cable groove 96 defined in a lower surface of the lower cam member 28b and an upper surface of the lower coupling member 37b (FIG. 6). From the firing cable groove 96, the firing cable 81 passes around the rotation post 38b of the lower coupling member 38b (FIG. 6), extends through the end effector 30, and is attached to the sled 94.

As the carriage 18 is advanced through the connector 23 (FIG. 2), the carriage 18 moves within the firing gap 84 of the firing rod 82 until a firing surface 18a (FIG. 25) of the carriage 18 engages the distal firing flag 83b of the firing rod 82. The distance between the firing surface 18a of the carriage 18 and the distal flag 83b, indicated by dimension G, defines a clamping dwell or delay for advancing the firing rod 82 in response to advancement of the carriage 18. The clamping dwell is at least equal to the distance required to advance the clamping shaft 62 to a position where the clamping hook 67 is past the clamping pivot arm 68 as shown in FIG. 18, such that the clamping pivot arm 68 is in the clamped position, as detailed above. In other words, the clamping dwell prevents the firing rod 82 from being advanced before the fastener and retainer jaws 32, 34 are in the clamped configuration. When the loading unit 10 is attached to a manually actuated handle, the clamping dwell is equal to a first pull of a trigger or moveable handle such that a subsequent pull of the trigger or moveable handle ejects fasteners 148b from the fastener cartridge 146 as the sled 94 translates through the fastener jaw 32.

With the end effector 30 in the clamped configuration (FIG. 20), the carriage 18 is advanced such that the firing surface 18a engages the distal flag 83b of the firing rod 82 to advance the firing rod 82 in the direction indicated by the arrow B (FIG. 27). As the firing rod 82 is advanced, the firing rod 82 tensions the firing cable 81, which is secured to the distal finger 87 of the firing rod 82, about the firing pulley 91 to pull the firing cable 81 in the direction indicated by arrow C. As the firing cable 81 is tensioned about the firing pulley 91, the firing cable 81 pulls the sled 94 proximally through the sled channel 141 of the fastener cartridge 146 to eject the fasteners 148b from the fastener cartridge 146 as detailed below.

Figure 30:
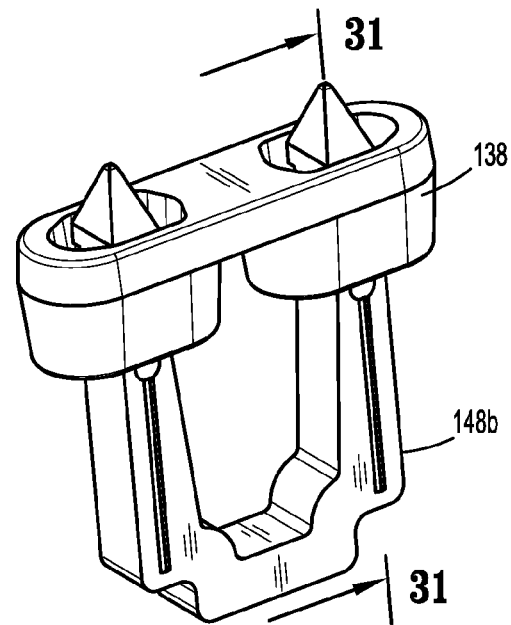
FIG. 30 is a perspective view of a completed two-part fastener of FIG. 29B.
Figure 31:
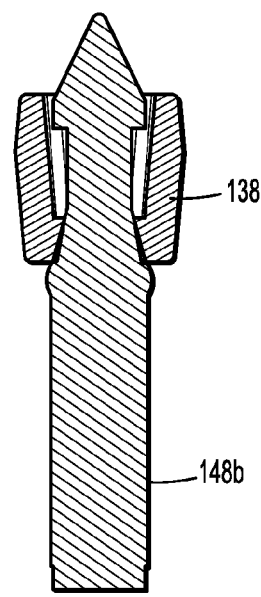
FIG. 31 is a cross-sectional view taken along the section line 31-31 of FIG. 30.

With reference to FIGS. 28A-29B, in an initial position (FIGS. 28A and 28B), the sled 94 is retained in an unfired or distal position adjacent a distal end of the fastener jaw 32 and each of the fasteners 148b is positioned within the fastener cartridge 146. As the sled 94 is pulled proximally through the sled channel 141 in the direction indicated by arrow F (FIG. 28A), an angled surface 95 of the sled 94 engages camming surface of the pushers 148a to move the pushers 148a towards the retainer jaw 34. Each pusher 148a is engaged with one or more fasteners 148b to eject the one or more fasteners 148b from the fastener cartridge 146 towards the retainer cartridge 136. As shown in FIGS. 30 and 31, each fastener 148b engages one of the retainers 138 to form a two-part fastener through tissue clamped between the fastener and retainer cartridges 146, 136.

In any of the embodiments disclosed herein, the fasteners 148b may be unformed staples and the retainer jaw 32 may include an anvil (not shown). In such embodiments, the fasteners 148b are ejected from the fastener cartridge 146 such that the fasteners 148b interact with the anvil to form staples through tissue clamped between the fastener cartridge 146 and the anvil (i.e., deform legs of the unformed staples). The articulation mechanism and/or firing mechanism disclosed above may be used in a device for firing deformable staples rather than the two-part fasteners discussed above.

In some embodiments, the sled 94 is positioned in a proximal portion of the fastener jaw 32 adjacent the proximal tab 142 and is pulled distally by the firing cable 81 as the firing cable 81 is tensioned. In such embodiments, the firing cable 81 passes around a post (not shown) that is positioned in a distal portion of the fastener jaw 32 after passing around the rotation post 38b. It will be appreciated that in such embodiments the angled surface 95 of the sled 94 faces distally and the camming surfaces of the pushers 148a face proximally.

In certain embodiments, the sled 94 includes a knife (not shown), that extends through a knife slot (not shown) to sever tissue between the fastener and retainer jaws 32, 34 as the sled 94 is pulled through the sled channel 141. In particular embodiments, the knife (not shown) is separate from the sled 94 and is attached to the firing cable 81 independent of the sled 94.

Referring back to FIG. 26, after the fasteners 148b are ejected from the fastener cartridge 146, the carriage 18 is retracted such that the carriage 18 engages the proximal flag 83a of the firing rod 82 to retract the firing rod 82. As the firing rod 82 is retracted, the tension in the firing cable 81 is released such that the firing cable 81 is slack within the inner housing 20. As the tension is released from the firing cable 81, the sled 94 remains in position within the fastener cartridge 146.

Referring now to FIGS. 32-35, the loading unit 10 is provided with a shipping lock 40 to secure the end effector 30 in a shipping configuration (FIG. 1). In the shipping configuration, the end effector 30 is articulated relative to the elongated body 12 and the retainer jaw 34 is spaced-apart from the fastener jaw 32. As shown in FIG. 1, in the shipping configuration, the end effector 30, including the fastener and retainer jaws 32, 34, is articulated about 45° with respect to the elongated body 12; however, it is contemplated that in the shipping configuration the end effector 30 may be articulated in a range of about 15° to about 60° with respect to the elongated body 12. Further, in the shipping configuration, the retainer jaw 34 is spaced-apart from the fastener jaw 32.

It is contemplated that in the shipping configuration, the retainer jaw 34 may be in any open position (i.e., between the open configuration and the clamped configuration) that allows for the retainer cartridge 136 and the fastener cartridge 146 to be coupled and decoupled from the retainer jaw 34 and the fastener jaw 32, respectively. As detailed below, in the shipping configuration, the clamping shaft 62 is fixed in a shipping position between its open and clamped positions. In the shipping position of the clamping shaft 62, the clamping sleeve 76 is advanced over the upper and lower cam members 28a, 28b such that portions or the fastener and retainer jaws 32, 34 (e.g., proximal tabs 132, 142) engage the jaw support 78. In the shipping configuration, the clamping sleeve 76 prevents the fastener and retainer jaws 32, 34 from moving towards the open configuration and the jaw support 78 prevents the fastener and retainer jaws 32, 34 from moving towards the clamped configuration.

With particular reference to FIGS. 33-35, the articulation rod 52 defines the articulation locking notch 55 and the clamping shaft 62 defines the clamping locking notch 66. In the shipping configuration, each of the locking notches 55, 66 is engaged by a respective locking finger 45, 46 of the shipping lock 40. Specifically, an articulation locking finger 45 of the shipping lock 40 engages the articulation locking notch 55 of the articulation rod 52 and a clamping locking finger 46 of the shipping lock 40 engages the clamping locking notch 66 of the clamping shaft 62. The engagement of the locking fingers 45, 46 with the locking notches 55, 66 fixes the orientation of the end effector 30 with respect to the elongated body 12 and fixes the fastener and retainer jaws 32, 34 in the shipping configuration as detailed above. By fixing the orientation of the end effector 30 and position of the fastener and retainer jaws 32, 34, the fastener cartridge 146 and the retainer cartridge 136 can be coupled and decoupled from the fastener jaw 32 and the retainer jaw 34, respectively, without moving the articulation assembly 50, the clamping mechanism 60, and the firing mechanism 90. Further, by fixing the orientation of the end effector 30 and position of the fastener and retainer jaws 32, 34, the loading unit 10 may be attached and detached from a surgical instrument without unintentional movement of the end effector 30. It is contemplated that the shipping lock 40 may also include support fingers 47 to support the shipping lock 40 on the proximal tube 14 of the elongated body 12.

With reference to FIGS. 1, 36, and 37, the shipping lock 40 is secured to the loading unit 10 by a locking ring 42 engaged with a hook 41 of the shipping lock 40. The locking ring 42 includes a locking shelf 43 and proximal fingers 44. The locking ring 42 is rotatably positioned over the connector 23 of the inner housing 20. In a locked position of the locking ring 42 (FIGS. 1 and 35), the locking shelf 43 of the locking ring 42 engages the hook 41 of the shipping lock 40 to secure the shipping lock 40 to the loading unit 10. When the loading unit 10 is coupled to an adapter (not shown) or a surgical instrument (not shown), the connector 23 is secured to the adapter or surgical instrument by a bayonet type connection such that the adapter or surgical instrument engages the proximal fingers 44 of the locking ring 42 to rotate the locking ring 42 to an unlocked position (FIG. 37) such that the locking shelf 43 is rotated out of engagement with the hook 41. With the locking ring 42 in the unlocked position, a release tab 48 of the shipping lock 40 is engaged to remove the shipping lock 40 from the loading unit 10.

Referring now to FIGS. 38-43, the loading unit 10 is used during a Total Laparoscopic Hysterectomy (TLH) procedure to close the vaginal cuff VC in accordance with the present disclosure. While this is an example of one procedure that may be performed using the loading unit 10, it is contemplated that other procedures may also be performed using the loading unit 10. To begin, the loading unit 10 is loaded by coupling a fastener cartridge 146 and a retainer cartridge 136 to the fastener and retainer jaws 32, 34, respectively. The loading unit 10 may be supplied in a preloaded condition or may be supplied in a kit with one or more pairs of fastener and retainer cartridges with varying lengths and types of fasteners (e.g., 2 mm, 3 mm, 3.5 mm, 4 mm, 4.5 mm, 5 mm, 5.5 mm, etc., two-part fasteners or deformable staples). With the fastener and retainer cartridges 136, 146 coupled to the fastener and retainer jaws 32, 34, respectively, the loading unit 10 is attached to a surgical instrument (not explicitly shown). When the loading unit 10 is attached to the surgical instrument, the locking ring 42 is rotated from a locked position to an unlocked position. With the locking ring 42 in the unlocked position, the release tab 48 is engaged to remove the shipping lock 40 from the loading unit 10. It is contemplated that the loading unit 10 may be attached to the surgical instrument before the fastener and retainer cartridges 136, 146 are coupled to the fastener and retainer jaws 32, 34, respectively.

With the shipping lock 40 removed from the loading unit 10, the end effector 30 is articulated to a straight configuration relative to the elongated body 12 such that the fastener and retainer jaws 32, 34 are substantially aligned with the elongated body 12. In addition, clamping shaft 62 (FIG. 14) is retracted to its open position such that the clamping sleeve 76 (FIG. 1) is retracted to its proximal position. When the clamping shaft 62 is in its open position, the end effector biasing member 31 (FIG. 4) biases the fastener and retainer jaws 32, 34 away from one another to an open configuration.

Figure 38:
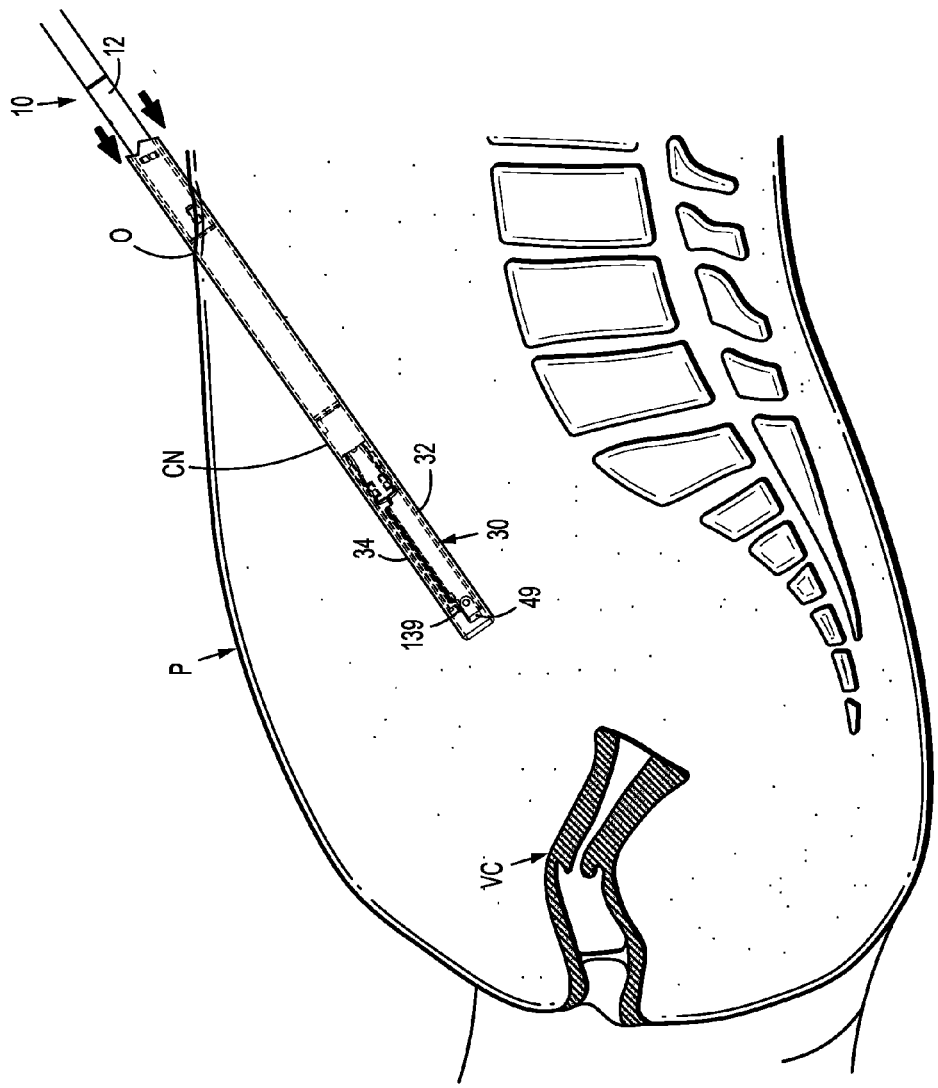
FIG. 38 is a cut-away view of the loading unit of FIG. 1 in use during a surgical procedure in accordance with the present disclosure with the loading unit in a straight configuration.

With particular reference to FIG. 38, with the end effector 30 in the straight configuration, the loading unit 10 is inserted through a cannula CN that is positioned in an opening O (e.g., an incision or a naturally occurring orifice) of a patient P to access a vaginal cuff VC. When the loading unit 10 is inserted into the cannula CN, the inner surfaces of the cannula CN may engage the outer surfaces of the fastener and retainer jaws 32, 34 to move the fastener and retainer jaws 32, 34 towards one another against the end effector biasing member 31 such that the end effector 30 is substantially cylindrical along its length and has a substantially uniform outer diameter. Additionally or alternatively, the fastener and retainer jaws 32, 34 may be moved to the clamped configuration and the locking member 49 may be rotated over the locking fingers 139 of the retainer jaw 32 to secure the fastener and retainer jaws 32, 34 in the clamped configuration. It is contemplated that the fastener and retainer jaws 32, 34 may be moved to the clamped configuration by engaging the inner surfaces of the cannula CN, by being manually closed by a clinician pinching the fastener and retainer jaws 32, 34 together, or by advancing the clamping sleeve 76 to its distal position by advancing the clamping shaft 62 to its clamped position.

Figure 39:
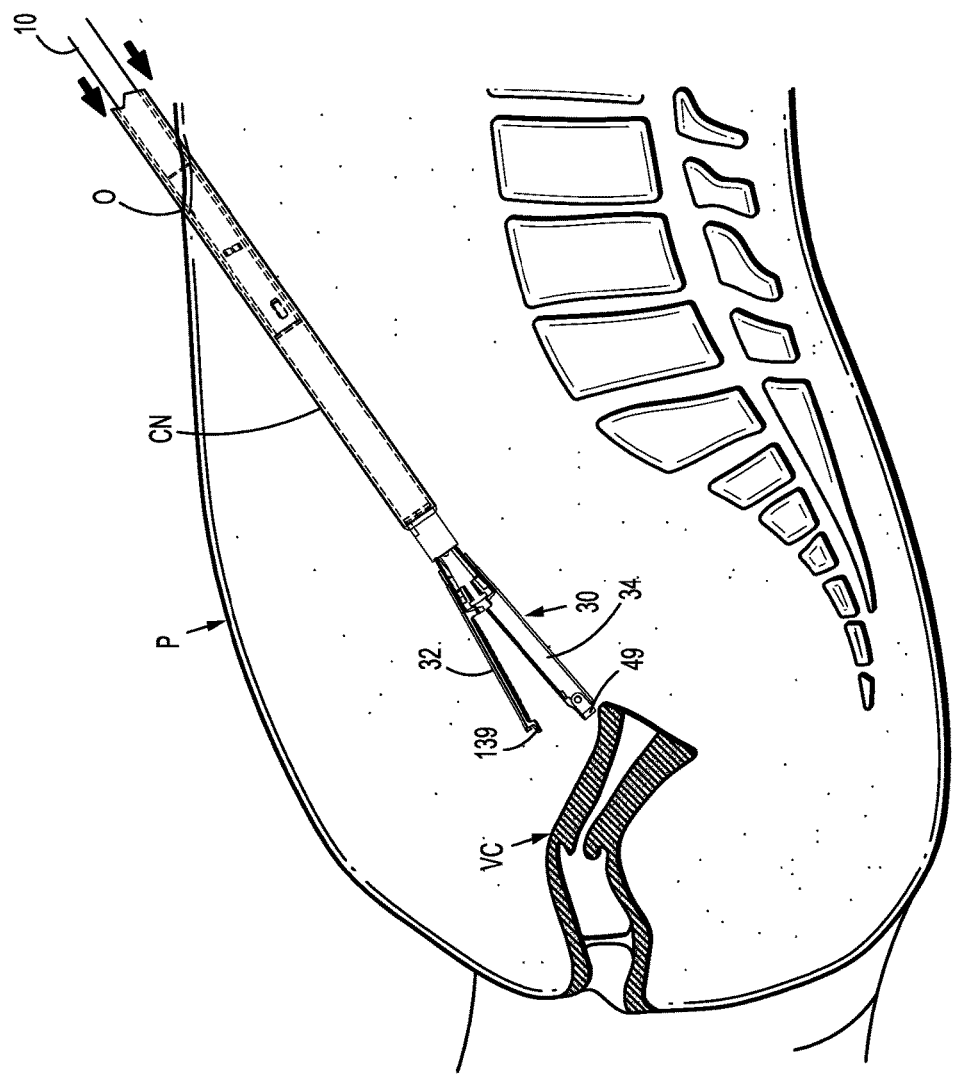
FIG. 39 is a cut-away view of the loading unit of FIG. 38 with the end effector extending past a distal end of the cannula and in a straight, open configuration.
Figure 40:
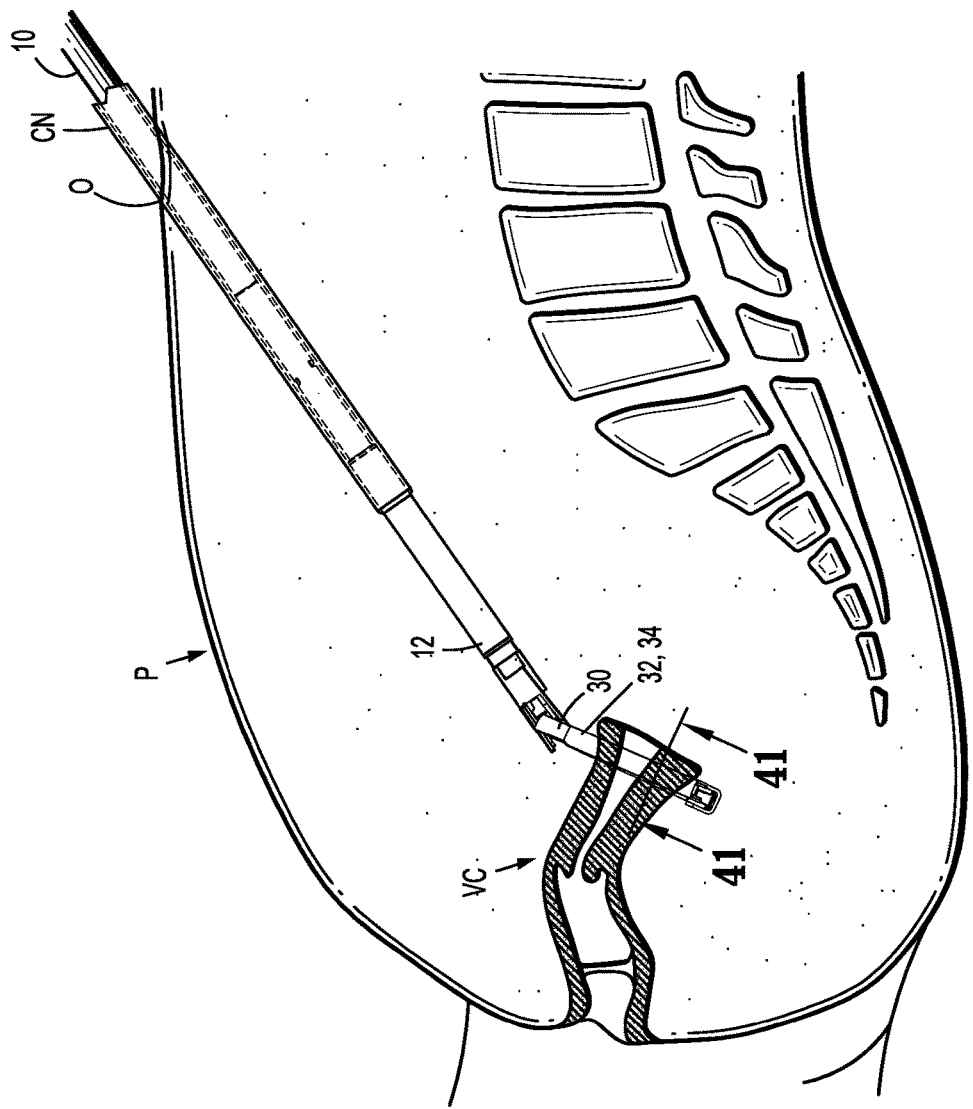
FIG. 40 is a cut-away view of the loading unit of FIG. 39 in a fully articulated, open configuration with a vaginal cuff positioned between the jaws of the end effector.
Figure 41:
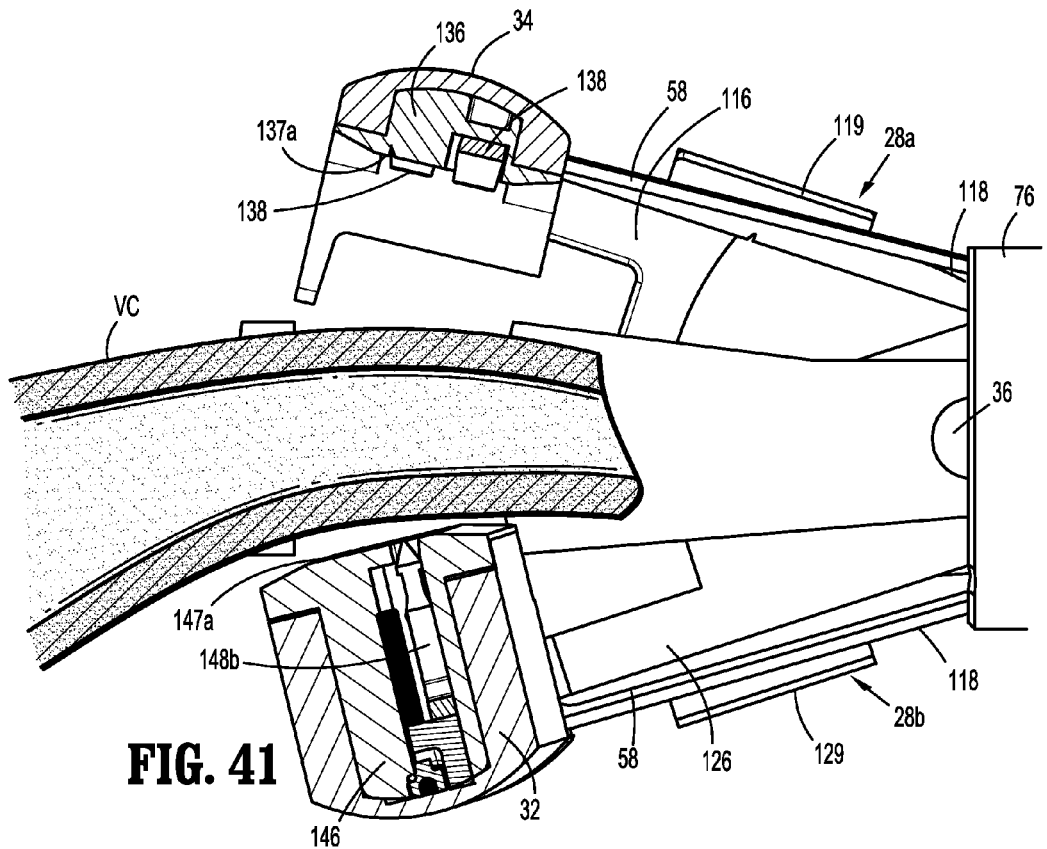
FIG. 41 is a cross-sectional view taken along the section line 41-41 of FIG. 40.
Figure 42:
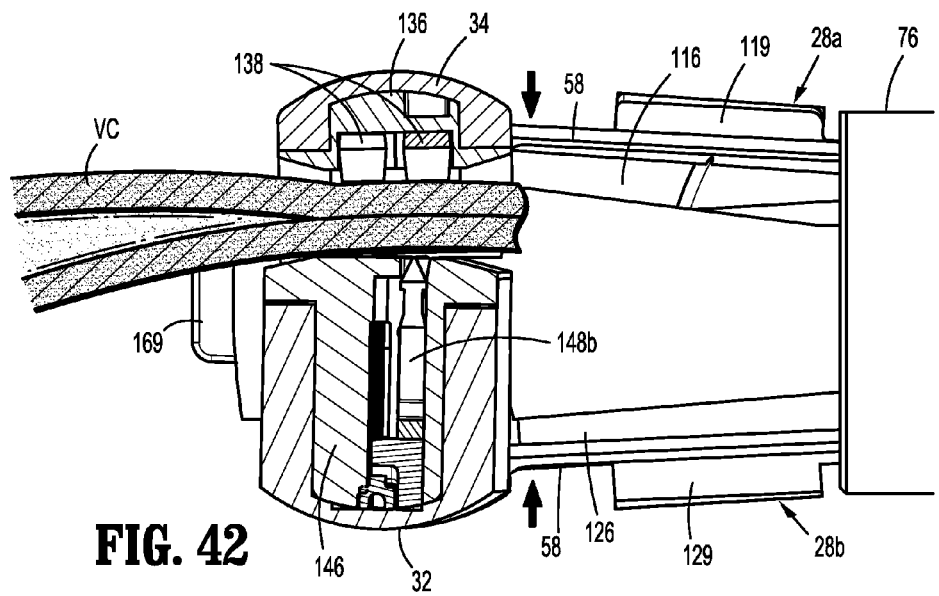
FIG. 42 is a cross-sectional view of the end effector of FIG. 41 in a clamped configuration.

Referring now to FIGS. 39 and 40, the fastener and retainer jaws 32, 34 are positioned adjacent an open end of the vaginal cuff VC and the end effector 30 is articulated to the fully articulated configuration. It will be appreciated that if the fastener and retainer jaws 32, 34 are in a clamped configuration, the locking member 49 must be rotated from over the locking fingers 139 of the retainer jaw 32 and the clamping mechanism 60 must be moved to its open position before the end effector 30 may be articulated. In the fully articulated configuration, the fastener and retainer jaws 32, 34 of the end effector 30 are substantially perpendicular to the open end of the vaginal cuff VC. The fastener and retainer jaws 32, 34 are then moved over the vaginal cuff VC such that the vaginal cuff VC is positioned between the tissue contacting surfaces 137a, 147a of the fastener and retainer jaws 32, 34. The loading unit 10 is then manipulated to advance the carriage 18 to move the clamping mechanism 60 from its open position to its clamped position. As the vaginal cuff VC is positioned between the jaws 32, 34, the vaginal cuff VC may be flattened between the tissue contacting surfaces 137a, 147a of the fastener and retainer jaws 32, 34. It will be appreciated, that the tissue contacting surfaces 137a, 147a of the fastener and retainer jaws 32, 34 remain substantially parallel to one another as the fastener and retainer jaws 32, 34 are moved to the clamped configuration.

With the vaginal cuff VC clamped between the fastener and retainer jaws 32, 34, a clinician verifies that the open end of the vaginal cuff VC is between the fastener and retainer jaws 32, 34. The locking member 49 may be rotated over the locking fingers 139 of the retainer jaw 34 to secure the fastener and retainer jaws 32, 34 in the clamped configuration. When the locking member 49 is rotated over the locking fingers 139, the locking member 49 closes the distal end of the fastener and retainer jaws 32, 34 such that the vaginal cuff VC remains between the fastener and retainer jaws 32, 34. The locking member 49 may be rotated over the locking fingers 139 by engaging the locking member 49 with another surgical instrument (not shown).

With the vaginal cuff VC clamped between the fastener and retainer jaws 32, 34, the loading unit 10 is manipulated to advance the carriage 18 to engage the firing mechanism 80 such that the sled 94 is pulled through the fastener cartridge 146 to drive the fasteners 148b towards the retainers 138 to form two-part fasteners, as detailed above, to close the vaginal cuff VC. Alternatively, as detailed above, the fasteners 148b may be deformable staples that are deformed to form staples for closing the vaginal cuff VC. The fasteners 148b and the retainers 138 may be bioabsorbable such that the fasteners 148b and retainers 138 are absorbed as the anastomosis of the vaginal cuff VC is completed. It is contemplated that the fasteners 148b and the retainers 138 may be coated with a substance that aids in the anastomosis of the vaginal cuff VC.

Figure 43:
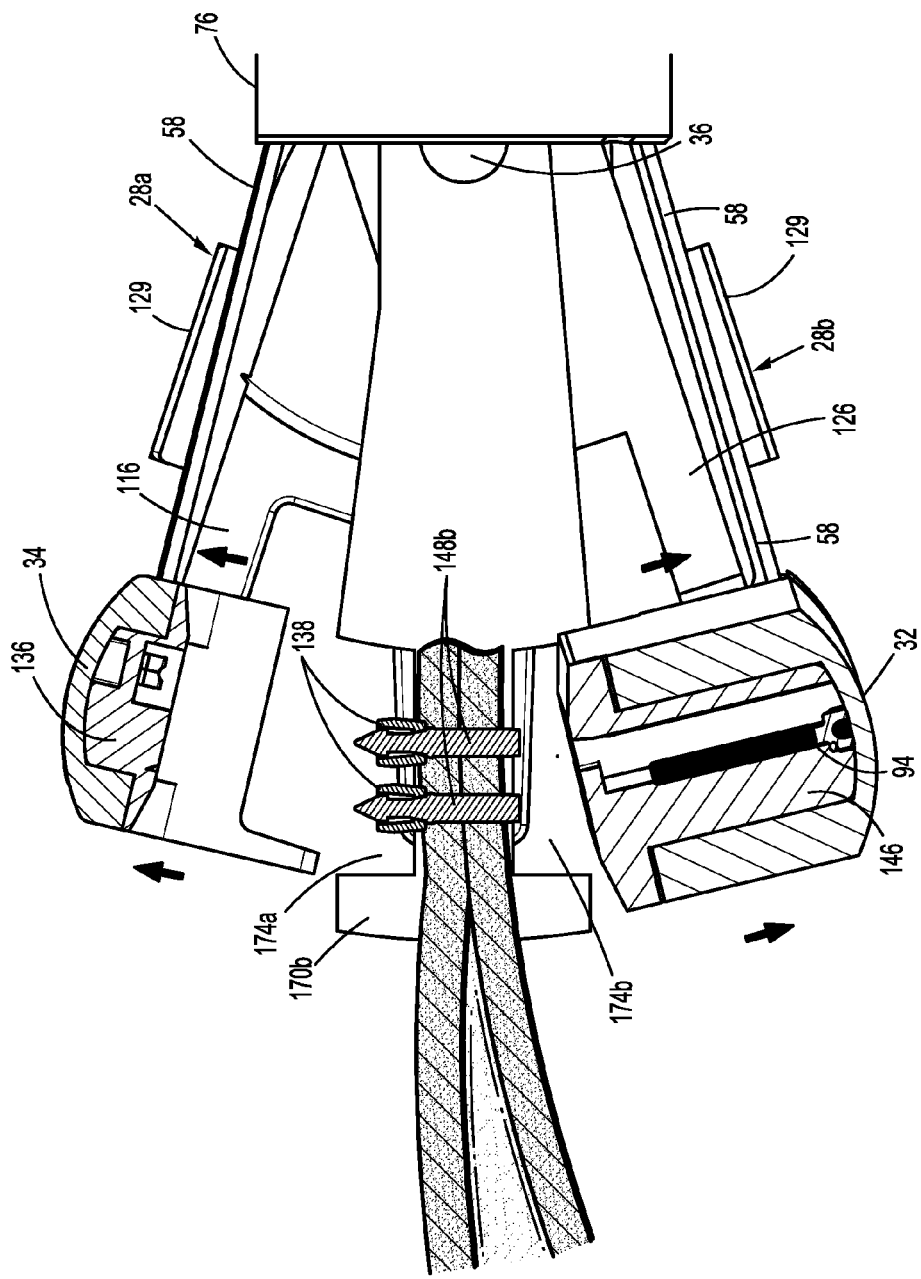
FIG. 43 is a cross-sectional view of the end effector of FIG. 42 in an open configuration after the fasteners have been fired through the vaginal cuff.

Referring to FIG. 43, after the fasteners 148b are ejected through the vaginal cuff VC, the clamping mechanism 60 is moved to its open position and the locking member 49 is rotated from over the locking fingers 139 of the retainer jaw 34 to permit the fastener and retainer jaws 32, 34 to return to the open configuration. As the fastener and retainer jaws 32, 34 return to the open configuration, the vaginal cuff VC is released from between the fastener and retainer jaws 32, 34. The end effector 30 is then articulated to the straight configuration such that the fastener and retainer jaws 32, 34 are substantially aligned with the elongated body 12. With the fastener and retainer jaws 32, 34 in the straight configuration, the loading unit 10 is withdrawn from the surgical site through the cannula CN. It will be appreciated that as the loading unit 10 is withdrawn the straight configuration, the inner surface of the cannula CN may engage the outer surfaces of the fastener and retainer jaws 32, 34 to move the fastener and retainer jaws 32, 34 towards one another against the end effector biasing member 31.

After the loading unit 10 is withdrawn from the surgical site, the loading unit 10 may be detached from the surgical instrument. With the loading unit 10 separated from surgical instrument, the loading unit 10 may be sterilized for reuse in another surgical procedure.

Alternatively, the loading unit 10 may be reloaded by positioning loading unit 10 in the shipping configuration (i.e., articulating the end effector 30 to the shipping configuration and moving the clamping mechanism 60 to its shipping position). With the loading unit 10 in the shipping configuration, the shipping lock 40 may be coupled about the proximal tube 14 to fix the loading unit 10 in the shipping configuration. With the loading unit 10 in the shipping configuration, the fastener cartridge 146 and the retainer cartridge 136 may be decoupled from the fastener and retainer jaws 32, 34, respectively. Then, a new fastener cartridge and retainer cartridge may be coupled to the fastener and retainer jaws 32, 34, respectively, such that the loading unit 10 may be reused during the same surgical procedure.

While the loading unit 10 is detailed above for performing a TLH, it is contemplated that the loading unit 10 may be used for closing a variety of tubular structures including, but not limited to, veins, arteries, and bowels.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope of the claims appended hereto.

What is claimed:

1. An end effector comprising:
   a first jaw member including:
      a first camming member defining a first rotation hole and a first pivot hole;
      a first body having a first proximal tab defining a first rotation opening and a first articulation opening; and
      a first coupling member having a first rotation post and a first articulation post, the first rotation post inserted in the first rotation hole and the first rotation opening, the first articulation post positioned within the first articulation opening;
   a second jaw member including:
      a second camming member defining a second rotation hole and a second pivot hole;
      a second body having a second proximal tab defining a second rotation opening and a second articulation opening; and
      a second coupling member having a second rotation post and a second articulation post, the second rotation post inserted in the second rotation hole and the second rotation opening, the second articulation post positioned within the second articulation opening; and
   a pivot pin positioned in the first and second pivot holes, the first and second jaw members pivotable relative to one another between an open configuration and a clamped configuration about the pivot pin in a parallel manner, the first and second bodies articulatable relative to the first and second camming members about the first and second articulation posts.

2. The end effector according to claim 1, wherein the first and second rotation holes are distal of the first and second pivot holes.

3. The end effector according to claim 1, wherein the first rotation hole is orthogonal to the first pivot hole and the second rotation hole is orthogonal to the second pivot hole.

4. The end effector according to claim 1, wherein the first camming member includes first sidewalls that define the first pivot hole and the second camming member includes second sidewalls that define the second pivot hole.

5. The end effector according to claim 4, wherein the second sidewalls define a channel, the first sidewalls inserted in the channel to axially align the first and second pivot holes.

6. The end effector according to claim 4, wherein the first camming member includes a first support arm extending distally from the first sidewalls which defines the first rotation hole, and wherein the second camming member includes a second support arm extending distally from the second sidewalls which defines the second rotation hole.

7. The end effector according to claim 1, wherein first body includes a distally extending locking finger and the second body includes a locking member rotatably coupled to a distal end thereof, the locking member rotatable over the locking finger when the first and second jaw members are in the clamped configuration to maintain the first and second jaw members in the clamped configuration.

8. The end effector according to claim 1, wherein in the first and second bodies are articulatable between a straight configuration such that the first and second bodies are longitudinally aligned with the first and second camming members and a fully articulated configuration such that the first and second bodies define an angle with the first and second camming members.

9. The end effector according to claim 8, wherein the fully articulated configuration is defined by the first and second bodies being articulated in a range of 75° to 105° from the first and second camming members.

10. A loading unit comprising:
an end effector including:
a first jaw member having:
a first camming member defining a first rotation hole and a first pivot hole, the first rotation hole orthogonal to and distal of the first pivot hole;
a first body having a first proximal tab defining a first rotation opening and a first articulation opening; and
a first coupling member having a first rotation post and a first articulation post, the first rotation post inserted in the first rotation hole and the first rotation opening, the first articulation post positioned within the first articulation opening;
a second jaw member having:
a second camming member defining a second rotation hole and a second pivot hole, the second rotation hole orthogonal to and distal of the second pivot hole;
a second body having a second proximal tab defining a second rotation opening and a second articulation opening; and
a second coupling member having a second rotation post and a second articulation post, the second rotation post passing through the second rotation hole and the second rotation opening, the second articulation post positioned within the second articulation opening; and
a pivot pin positioned in the first and second pivot holes; and
a housing including:
a connector positioned at a proximal end of the housing, the connector configured to couple the loading unit to a surgical instrument, the housing defining a longitudinal axis;
a clamping mechanism operatively associated with the first and second camming members to pivot the first and second jaw members relative to one another about the pivot pin between an open configuration and a clamped configuration; and
an articulation mechanism operatively associated with the first and second coupling members to articulate the first and second bodies about the first and second articulation posts between a straight configuration and a fully articulated configuration.

11. The loading unit according to claim 10, wherein the articulation mechanism includes first and second articulation rods, a distal end of the first articulation rod coupled to the first articulation post and a distal end of the second articulation rod coupled to the second articulation post.

12. The loading unit according to claim 11, wherein the articulation mechanism includes an articulation pivot arm having a first pivot, a second pivot, and a third pivot, the first pivot is positioned at a first end of the articulation pivot arm and is rotatably supported within the housing, the third pivot is positioned at a second end of the articulation pivot arm and is coupled to proximal ends of the first and second articulation rods, the second pivot positioned between the first and second ends of the articulation pivot arm.

13. The loading unit according to claim 12, wherein the articulation mechanism includes an articulation shaft having a distal end coupled to the second pivot and a proximal end positioned adjacent the connector of the housing, the first and second bodies adapted to articulate between the straight and articulated configurations in response to longitudinal translation of the articulation shaft.

14. The loading unit according to claim 13, wherein the articulation shaft has a proximal flag adjacent the connector of the housing which is configured to be engaged by a surgical instrument.

15. The loading unit according to claim 10, wherein the clamping mechanism moves the first and second bodies towards the clamped configuration in a parallel manner when the first and second jaw members are in the fully articulated configuration.

16. The loading unit according to claim 10, wherein the first and second camming members each include a camming surface, and wherein the clamping mechanism includes a clamping sleeve having a distal end, the clamping sleeve positioned about the first and second camming members, the clamping sleeve longitudinally translatable between a proximal position and a distal position, the clamping sleeve engaging the camming surfaces of the first and second camming members as the clamping sleeve is translated towards the distal position to pivot the first and second jaw members towards the clamped position.

17. The loading unit according to claim 16, wherein the first and second camming members each include a clamp stop at a distal end of the camming surfaces, the clamping sleeve abutting the clamp stop when the clamping sleeve is in the distal position.

18. The loading unit according to claim 17, wherein the clamp stops are positioned proximal to the first and second pivot holes.

19. The loading unit according to claim 17, wherein the clamp stops are positioned proximal to the first and second rotation posts.

20. The loading unit according to claim 17, wherein the clamp stops are positioned proximal to the pivot pin.

21. The loading unit according to claim 16, wherein portions of the camming surfaces of the first and second camming members extend proximally of the first and second pivot holes.

22. The loading unit according to claim 16, wherein portions of the camming surfaces of the first and second camming members extend proximally of the first and second rotation posts.

23. The loading unit according to claim 16, wherein portions of the camming surfaces of the first and second camming members extend proximally of the pivot pin.

24. The loading unit according to claim 16, wherein the clamping mechanism includes:
a clamping pivot arm having a first end rotatably supported within the housing, a second end, and a cam follower positioned between the first and second ends;
a clamping rod having a distal end operatively coupled to the clamping sleeve and a proximal end coupled to the second end of the clamping pivot arm; and
a clamping shaft having a clamping hook positioned at a distal end of the clamping shaft, the clamping hook engaging the cam follower of the clamping pivot arm to rotate the clamping pivot arm about its first end to move the clamping sleeve between the proximal and distal positions in response to longitudinal translation of the clamping shaft, the clamping shaft having a proximal end positioned adjacent the connector of the housing and configured to be engaged by the surgical instrument.

* * * * *